United States Patent
Anceriz et al.

(10) Patent No.: US 10,736,963 B2
(45) Date of Patent: Aug. 11, 2020

(54) METHODS FOR DETECTING TISSUE INFILTRATING NK CELLS

(71) Applicant: INNATE PHARMA, Marseilles (FR)

(72) Inventors: Nadia Anceriz, Marseilles (FR); Cecile Bonnafous, Marseilles (FR); Arnaud Dujardin, Marseilles (FR); Carine Paturel, Marcy l'Etoile (FR)

(73) Assignee: INNATE PHARMA, Marseilles (FR)

( * ) Notice: Subject to any disclaimer, the term of this patent is extended or adjusted under 35 U.S.C. 154(b) by 216 days.

(21) Appl. No.: 15/747,190

(22) PCT Filed: Jul. 4, 2016

(86) PCT No.: PCT/EP2016/065653
§ 371 (c)(1),
(2) Date: Jan. 24, 2018

(87) PCT Pub. No.: WO2017/016805
PCT Pub. Date: Feb. 2, 2017

(65) Prior Publication Data
US 2018/0369373 A1    Dec. 27, 2018

Related U.S. Application Data

(60) Provisional application No. 62/196,409, filed on Jul. 24, 2015.

(51) Int. Cl.
| | | |
|---|---|---|
| A61K 39/00 | (2006.01) | |
| A61K 39/395 | (2006.01) | |
| G01N 33/566 | (2006.01) | |
| G01N 33/574 | (2006.01) | |
| C07K 16/28 | (2006.01) | |
| A61P 35/00 | (2006.01) | |

(52) U.S. Cl.
CPC ........ A61K 39/39558 (2013.01); A61P 35/00 (2018.01); C07K 16/2803 (2013.01); G01N 33/566 (2013.01); G01N 33/57484 (2013.01); G01N 2333/70596 (2013.01)

(58) Field of Classification Search
None
See application file for complete search history.

(56) References Cited

U.S. PATENT DOCUMENTS

| | | | |
|---|---|---|---|
| 6,979,546 B2 | 12/2005 | Moretta et al. | |
| 7,074,409 B2 | 7/2006 | Moretta et al. | |
| 7,138,243 B2 | 11/2006 | Moretta et al. | |
| 7,279,291 B2 | 10/2007 | Moretta et al. | |
| 7,517,966 B2 | 4/2009 | Moretta et al. | |
| 7,732,131 B2 | 6/2010 | Moretta et al. | |
| 7,803,376 B2 | 9/2010 | Velardi et al. | |
| 8,119,775 B2 | 2/2012 | Moretta et al. | |
| 8,388,970 B2 | 3/2013 | Padkaer et al. | |
| 8,465,931 B2 | 6/2013 | Moretta et al. | |
| 8,614,307 B2 | 12/2013 | Moretta et al. | |
| 8,981,065 B2 | 3/2015 | Moretta et al. | |
| 8,993,319 B2 | 3/2015 | Moretta et al. | |
| 9,018,366 B2 | 4/2015 | Padkaer et al. | |
| 9,067,997 B2 | 6/2015 | Romagne et al. | |
| 9,090,876 B2 | 7/2015 | Velardi et al. | |
| 9,447,185 B2 | 9/2016 | Romagne et al. | |
| 9,708,403 B2 | 7/2017 | Padkaer et al. | |
| 9,789,182 B2 | 10/2017 | Graziano et al. | |
| 9,844,593 B2 | 12/2017 | Andre et al. | |
| 10,059,765 B2 | 8/2018 | Velardi et al. | |
| 10,113,003 B2 | 10/2018 | Gauthier et al. | |
| 10,160,810 B2 | 12/2018 | Moretta et al. | |
| 10,174,112 B2 | 1/2019 | Bonnafous et al. | |
| 10,253,095 B2 | 4/2019 | Romagne et al. | |
| 10,329,348 B2 | 6/2019 | Andre et al. | |
| 10,344,087 B2 | 7/2019 | Bonnafous et al. | |
| 10,519,234 B2 | 12/2019 | Gauthier et al. | |
| 10,577,416 B2 | 3/2020 | Blery et al. | |
| 2005/0037002 A1 | 2/2005 | Velardi et al. | |
| 2005/0159332 A1 | 7/2005 | Moretta et al. | |
| 2005/0221438 A1 | 10/2005 | Moretta et al. | |
| 2006/0246068 A1 | 11/2006 | Moretta et al. | |
| 2007/0065875 A1 | 3/2007 | Moretta et al. | |
| 2007/0178106 A1 | 8/2007 | Romagne | |
| 2007/0231322 A1 | 10/2007 | Romagne et al. | |
| 2008/0063717 A1 | 3/2008 | Romagne et al. | |
| 2008/0081346 A1 | 4/2008 | Moretta et al. | |
| 2008/0196111 A1 | 8/2008 | Vivier et al. | |
| 2008/0248045 A1 | 10/2008 | Moretta et al. | |
| 2008/0274047 A1 | 11/2008 | Romagne et al. | |
| 2008/0305117 A1 | 12/2008 | Padkaer et al. | |
| 2009/0075340 A1 | 3/2009 | Padkaer et al. | |
| 2009/0081240 A1 | 3/2009 | Moretta et al. | |
| 2009/0196850 A1 | 8/2009 | Romagne et al. | |
| 2009/0208416 A1 | 8/2009 | Moretta et al. | |

(Continued)

OTHER PUBLICATIONS

Freud, A. G. et al. "Expression of the Activating Receptor, NKp46 (CD335), in Human Natural Killer and T-Cell Neoplasia" *American Journal of Clinical Pathology*, Nov. 13, 2013, pp. 853-866, vol. 140, No. 6.

Unknown, "NCR1 / NKP46 Mouse anti-Human Monoclonal (N1d9) Antibody—LS-B2105—LSBio" *Lifespan Biosciences, Inc.*, Aug. 21, 2014, retrieved on Aug. 26, 2016, retrieved from the Internet: URL:http://www.funakoshi.co.jp/data/datasheet/LSB/LS-B2105.pdf, pp. 1-2.

Platonova, S. et al. "Profound Coordinated Alterations of Intratumoral NK Cell Phenotype and Function in Lung Carcinoma" *Cancer Research*, Aug. 15, 2011, pp. 5412-5422, vol. 71, No. 16.

(Continued)

*Primary Examiner* — Michail A Belyavskyi
(74) *Attorney, Agent, or Firm* — Saliwanchik, Lloyd & Eisenschenk

(57) ABSTRACT

The present invention relates to methods for detecting and monitoring NK cells in paraffin-embedded tissue samples. Also provided are antibodies, antibody fragments, and derivatives thereof that specifically bind to NKp46 present on the surface of NK cells in paraffin-embedded tissue samples.

5 Claims, 3 Drawing Sheets
Specification includes a Sequence Listing.

(56) References Cited

U.S. PATENT DOCUMENTS

| | | |
|---|---|---|
| 2010/0015153 A1 | 1/2010 | Moretta et al. |
| 2010/0285531 A1 | 11/2010 | Moretta et al. |
| 2011/0008335 A1 | 1/2011 | Velardi et al. |
| 2011/0229486 A1 | 9/2011 | Moretta et al. |
| 2011/0293561 A1 | 12/2011 | Romagne et al. |
| 2012/0208237 A1 | 8/2012 | Moretta et al. |
| 2012/0328615 A1 | 12/2012 | Romagne et al. |
| 2013/0143269 A1 | 6/2013 | Padkaer et al. |
| 2013/0251711 A1 | 9/2013 | Andre et al. |
| 2013/0287770 A1 | 10/2013 | Moretta et al. |
| 2013/0315892 A1 | 11/2013 | Moretta et al. |
| 2014/0234342 A1 | 8/2014 | Narni-Mancinelli et al. |
| 2015/0125464 A1 | 5/2015 | Moretta et al. |
| 2015/0132316 A1 | 5/2015 | Moretta et al. |
| 2015/0191542 A1 | 7/2015 | Blery et al. |
| 2015/0191547 A1 | 7/2015 | Moretta et al. |
| 2015/0283234 A1 | 10/2015 | Graziano et al. |
| 2015/0299319 A1 | 10/2015 | Velardi et al. |
| 2015/0344576 A1 | 12/2015 | Moretta et al. |
| 2015/0376274 A1 | 12/2015 | Bonnafous et al. |
| 2015/0376275 A1 | 12/2015 | Romagne et al. |
| 2016/0002345 A1 | 1/2016 | Bonnafous et al. |
| 2016/0046712 A1 | 2/2016 | Padkaer et al. |
| 2016/0369002 A1 | 12/2016 | Gauthier et al. |
| 2017/0198038 A1 | 7/2017 | Gauthier et al. |
| 2017/0210802 A1 | 7/2017 | Gauthier et al. |
| 2017/0267764 A1 | 9/2017 | Blery et al. |
| 2017/0291947 A1 | 10/2017 | Andre et al. |
| 2017/0298131 A1 | 10/2017 | Andre et al. |
| 2017/0298132 A1 | 10/2017 | Bonnafous et al. |
| 2017/0306014 A1 | 10/2017 | Cornen et al. |
| 2017/0313773 A1 | 11/2017 | Andre et al. |
| 2017/0369573 A1 | 12/2017 | Gauthier et al. |
| 2018/0117147 A1 | 5/2018 | Graziano et al. |
| 2018/0344829 A1 | 12/2018 | Cornen et al. |
| 2018/0355036 A1 | 12/2018 | Gauthier et al. |
| 2018/0369373 A1 | 12/2018 | Anceriz et al. |
| 2019/0031755 A1 | 1/2019 | Andre et al. |
| 2019/0048093 A1 | 2/2019 | Gauthier et al. |
| 2019/0055315 A1 | 2/2019 | Gauthier et al. |
| 2019/0085077 A1 | 3/2019 | Cornen et al. |
| 2019/0127463 A1 | 5/2019 | Bonnafous et al. |
| 2019/0135938 A1 | 5/2019 | Moretta et al. |
| 2019/0315857 A1 | 10/2019 | Bonnafous et al. |
| 2019/0322744 A1 | 10/2019 | Andre et al. |
| 2019/0322767 A1 | 10/2019 | Gauthier et al. |
| 2019/0367609 A1 | 12/2019 | Anceriz et al. |
| 2020/0048345 A1 | 2/2020 | Gauthier et al. |

OTHER PUBLICATIONS

Rusakiewicz, S. et al. "Immune Infiltrates Are Prognostic Factors in Localized Gastrointestinal Stromal Tumors" *Cancer Research*, Jun. 15, 2013, pp. 3499-3510, vol. 73, No. 12.

Sips, M. et al. "Altered distribution of mucosal NK cells during HIV infection" *Mucosal Immunology*, Jan. 2012, pp. 30-40, vol. 5, No. 1.

Written Opinion in International Application No. PCT/EP2016/065653, dated Nov. 8, 2016, pp. 1-9.

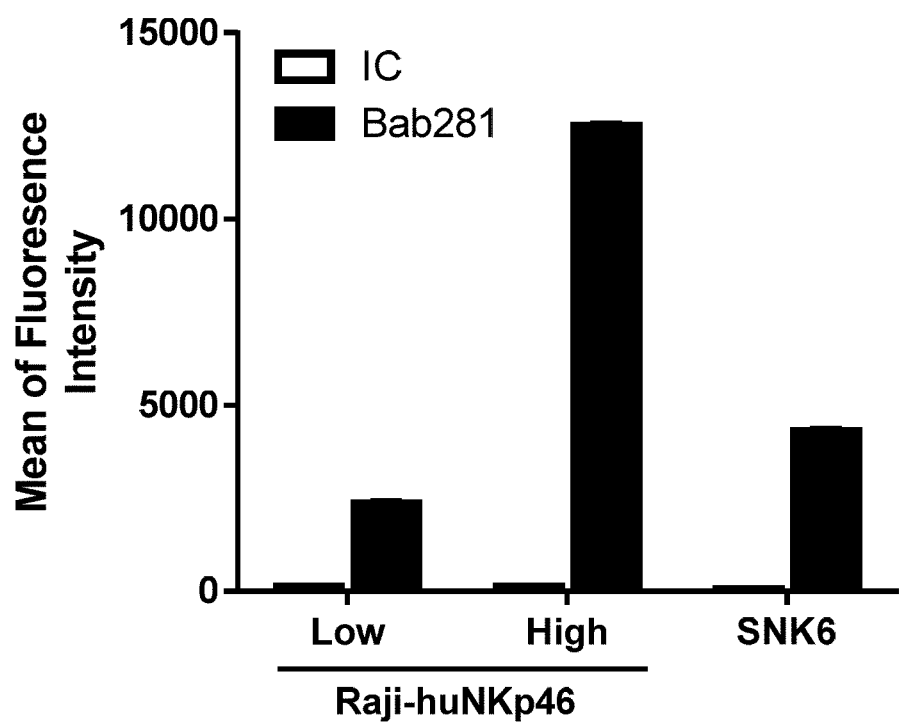

METHODS FOR DETECTING TISSUE INFILTRATING NK CELLS

CROSS-REFERENCE TO RELATED APPLICATIONS

This application is the U.S. national stage application of International Patent Application No. PCT/EP2016/065653, filed Jul. 4, 2016, which claims the benefit of U.S. Provisional Application No. 62/196,409 filed Jul. 24, 2015, the disclosures of which are incorporated herein by reference in their entirety; including any drawings and sequence listings.

REFERENCE TO THE SEQUENCE LISTING

The present application is being filed along with a Sequence Listing in electronic format. The Sequence Listing is provided as a file entitled "NKp46-5 PCT_ST25 txt", created Jun. 28, 2016, which is 7 KB in size. The information in the electronic format of the Sequence Listing is incorporated herein by reference in its entirety.

FIELD OF THE INVENTION

The present invention relates to research and diagnostic tools to detect tissue infiltrating NK cells in paraffin embedded tissue samples. The invention also relates to methods of using the tools to detect tissue-infiltrating NK cells, notably tumor-infiltrating, NK cells, as a discrete cell population and to combine detection with non-NK specific markers.

BACKGROUND

New methods of treatment of cancer are needed that are able to more specifically make use of the immune system to target cancer cells and, as such, avoid the side effects typical of traditional chemotherapeutic agents. In order to better understand the immune infiltrate, it is desirable to detect NK cells in patient tissue samples, for example to detect whether NK cells are infiltrating a tumor (or more generally any site of inflammation) and/or are present at the tumor periphery or otherwise in nearby tissue. This is typically done using frozen tissue samples. This is not only useful in research but can also help in the decision about what type of treatment to use, for example, by detecting whether a tissue (e.g. a tumor environment) is characterized by inflammation that includes NK cells and/or to characterize the type of immune cells present in a tissue (e.g. tumors, inflammatory disorders). The information can be valuable in order to select a treatment that is capable of modulating the activity of the available immune cells.

In addition to frozen tissue, markers can also be detected from tissue samples that have been preserved as formaldehyde (e.g. formalin)-fixed paraffin embedded (FFPE) samples. Following deparaffination, the slides are amenable to, e.g., immunohistochemical methods to detect the expression of specific proteins. The methods have been used routinely to detect tumor antigens in tumor tissue samples. Unfortunately, it is often impossible to find monoclonal antibodies that work effectively and with specificity in FFPE sections. This is believed to be due to the impact of the formalin fixation on structure of proteins. Epitopes bound by antibodies described as being specific on recombinant protein or cells are often present on other proteins when used in FFPE, rendering the antibodies non-specific. In other cases, many epitopes on native cellular protein are destroyed by formalin fixation, causing antibodies identified using recombinant protein or cells to be ineffective for staining FFPE sections.

In the field of oncology, tumor infiltrating T cells have been the subject of extensive study. Currently, multiplexed assays in FFPE sections permit study of T cell (using CD4 and CD8 as markers) and B cells (using CD20 as marker). Tumor infiltrating NK cells, however, despite reports of their existence, have received very little attention. Levi et al (2015) Oncotarget, Advance Publications 2015, page 1-9 used anti-CD56 antibody to stain tumor infiltrating cells. Typically, markers used to stain infiltrating lymphocytes do not permit straightforward detection of cells as a single lineage, leading to combination of multiple markers in an effort to estimate the types of cells present. Additionally, different cell populations express different markers as they mature. Consequently, assessing an immune profile in a tissue sample involves considerable uncertainty and/or requires ever greater number of markers to be assessed.

While antibodies to various proteins present on NK cells exist after many decades of study, such proteins are generally either have an expression that is not highly selective to NK cells, and the expression of many activating or inhibitory NK cell receptors is shared by at least some T cells or other immune cells. At the same time many receptors have not been amenable to generation of a ligand that binds with specificity in paraffin embedded sections (e.g., no specific epitope remains available following formalin fixation). As a result, there is a need for a way to unambiguously detect NK cells in paraffin embedded samples. The present invention addresses these and other needs.

SUMMARY OF THE INVENTION

The invention relates, inter alia, to the study and/or monitoring of NK cells in FFPE tissue samples. The invention relates to the detection of tissue-infiltrating human (and non-human primate) NK cells as a discrete cell population, and optionally to combine such detection with assessment of markers that are not unique to NK cells, including but not limited to other human Immunoglobulin Superfamily (IgSF) members. The markers that are not unique to NK cells may be present specifically on non-NK lineages, or may be present on non-NK lineages in addition to NK cells.

The present disclosure provides detection of tissue-infiltrating NK cells, including tumor-infiltrating NK cells, in FFPE samples using a single lineage specific and maturation-independent marker. In particular, NKp46 is expressed on tissue- and tumor-infiltrating NK cells present in FFPE samples, but not on non-NK cells in the tissue samples. Surprisingly, despite expression on NK cells of a wide range of non-lineage specific human Immunoglobulin Superfamily (IgSF) members, monoclonal antibodies can be distinguish the NK lineage-specific NKp46 from non-lineage specific IgSF members in FFPE. Accordingly new FFPE methods are provided in which NK cells are stained in a lineage-specific approach across substantially all populations of NK cells, including across stages of maturation, and across both $CD56^{bright}$ and $CD56^{dim}$ NK cells (as well as more generally across all population of cells or immune cells). The approach is particularly useful when conducting immune profiling in which cell populations are stained with non-lineage markers, notably markers that are also capable of being expressed by NK cells, e.g. other IgSF polypeptides. Provided also is antibody is available that permits cell lineage-specific detection of NK cells in FFPE sections that provides the ability to reliably distinguish NK cells from other lymphocyte populations or NK sub-populations.

The present disclosure arises from the characterization of anti-NKp46 antibodies and human tissue samples. Known anti-NKp46 antibodies do not stain, or lose specificity, in FFPE protocols. Through development of a screening protocol based on an assay that uses paraffin-embedded cell pellets expressing NKp46 and negative controls not expressing NKp46, the present authors obtained antibodies that recognize NKp46-specific epitopes in FFPE material were obtained. The antibodies permitted the staining and study of human FFPE tissue samples with specificity for human NKp46.

Further, the antibodies that recognize NKp46-specific epitopes in FFPE material also specifically recognize NKp46 in frozen tissue sections, as well as in cells in culture (e.g. in cytometry), and in Western Blot. The antibodies therefore provide the advantage of a single tool to be used in NKp46 detection across multiple types of sample preparation methodology and format.

The disclosure provides a monoclonal antibody that specifically binds a human NKp46 polypeptide, wherein said antibody specifically binds to said NKp46 polypeptide on cells in a biological sample that has been treated (or fixed) using formaldehyde (e.g. formalin, paraformaldehyde). Formaldehyde fixation is used in particular the preparation of paraffin embedded tissue sections which can then be deparaffinized and analysed for presence of a marker of interest, e.g. NKp46.

In another aspect, provided is a monoclonal antibody that specifically binds to NK cells in a paraffin embedded sample. Optionally, the antibody can be characterized by not binding to granulocytes, monocytes, B cells or T cells in an FFPE sample, or optionally any non-NK cells in an FFPE sample. Optionally, the antibody can be characterized by binding to $CD56^{bright}$ NK cells as well as $CD56^{dim}$ NK cells. Optionally, the antibody binds to an epitope on human NKp46 polypeptide present on NK cells in a paraffin embedded sample.

In one embodiment, unlike other monoclonal antibodies or polyclonal antibodies which can bind to shared epitopes on proteins other than NKp46 in FFPE samples (e.g. due to the appearance of epitopes due to the fixation process), the antibody of the disclosure can be characterized by not binding to any non-lineage specific IgSF family members (e.g. an IgSF member other than NKp46; a non-lineage specific natural cytotoxicity receptor such as NKp44 or NKp30).

In another aspect, provided is a monoclonal antibody that specifically binds to (a) NK cells in a paraffin embedded sample, (b) to NK cells in frozen tissue sample and (c) to NK cells in culture. Optionally the antibody further binds to NKp46 in under reducing conditions (e.g. in western blot). Optionally, the antibody can be characterized by not binding to non-NK cells, e.g., granulocytes, monocytes, B cells or T cells in an FFPE sample. Optionally, the antibody can be characterized by binding to $CD56^{bright}$ NK cells as well as $CD56^{dim}$ NK cells. Optionally, the antibody binds to an epitope on human NKp46 polypeptide present on NK cells in a paraffin embedded sample.

In another aspect, provided is a monoclonal antibody that specifically binds a human NKp46 polypeptide expressed by a cell that has been preserved in paraffin, e.g. a cell that has been preserved as a paraffin-embedded cell pellet. Optionally, the cells are pelleted, formaldehyde treated (e.g. formaldehyde, formalin, paraformaldehyde) and then paraffin embedded. Optionally, the cell that expresses the human NKp46 polypeptide is in a biological sample that has been deparaffinized prior to antibody binding and analysis.

The disclosure further provides a screening method based on formaldehyde-treated paraffin-embedded cell pellets (FFPE cell pellets) that reveal NKp46 epitopes present following formalin treatment. The methods can be used to identify antibodies that binds epitopes arise and/or are present on cellular NKp46 polypeptide following formalin treatment. Accordingly, in one aspect, the disclosure provides a monoclonal antibody that specifically binds NKp46 polypeptide-expressing cells (e.g. cells made to express NKp46) in a sample preserved as a paraffin-embedded cell pellet (and deparaffinized prior to analysis). Optionally the antibody is further characterized by not binding to NKp46-negative cells (cells that do not express NKp46) in a paraffin-embedded cell pellet. Optionally the antibody is further characterized by binding to NK cells in paraffin-embedded tissue sections.

Formaldehyde-fixed (e.g., formalin-fixed, paraformaldehyde-fixed), paraffin-embedded (FFPE) tissue provide two main advantages over other immunologic methods: (1) the tissue does not require special handling; and (2) cytologic and architectural features are well perceived, allowing for improved histopathologic interpretation. The present disclosure provides detecting the expression of human NK cells by immunostaining of paraffin-embedded tissue sections using antibody reagent that remains lineage-specific in FFPE. Consequently, rather than studying cytologic and architectural features of tissue from FFPE tissue separately from analysis of infiltrating immune cells, the present methods provides the possibility for a direct and/or combined analysis of NK cells in FFPE.

Using this method, thin sections of tissue (e.g., cancer tissue obtained by biopsy) can be obtained, fixed in e.g., formalin, embedded in paraffin, and then cut into very thin sections and mounted on slides. Following deparaffination, the slides are amenable to immunohistochemical methods to detect the expression of NKp46 using an anti-NKp46 antibody, providing a specific identification of NK cells among other immune cell populations. This method is particularly useful because it gives rise to methods to detect or identify the specific cellular and intracellular localization of NK cells.

The present disclosure provides novel compositions and methods involving antibodies and antibody fragments that allow specific binding to NKp46 within biological samples that have been treated with formalin, e.g., preserved as FFPE tissue. Such compositions and methods are useful for a multitude of applications, particularly for detecting (including quantifying) NK cells and NKp46 expression levels on NK cells in tissues, e.g., prior to anti-cancer or anti-inflammatory therapy, notably prior to immunotherapy. The antibodies disclosed herein can be used generally for detection (including quantification) and/or characterization of NK cells for research and diagnostic purposes, including but not limited to studying NK cells and/or their properties, activity, localization or migration. Immunohistochemistry studies of paraffin tissue sections can be used for example to assess the normal expression pattern of tissue antigens in NK cells and tissues; to diagnose hematopoietic disorders (e.g. to discriminate NK cells from other cells); to determine whether cellular antigens are lost from NK cells; identify changes in the expression of antigens associated with an NK cell; and identify the immune cell types (e.g., NK cells, NK cell subtypes) associated with a cancer or inflammatory lesion, or associated with an immune response or potential immune response in a cancer or inflammatory disorder. The antibodies disclosed herein can be used generally for detection and/or characterization of NK cells for prognostic tests to predict disease progression or treatment response, and in companion diagnostics to identify patients suitable for treatment with a particular therapeutic agent.

The method and reagents disclosed herein provide a specific marker of NK cells in samples that have been treated with formalin, notably those preserved as FFPE sections, and can be used as the sole marker to identify NK cells. However it will be appreciated that the reagents disclosed herein can also be used in other non-FFPE based methods to detect human NK cells, e.g., western blot, flow cytometry, IHC in frozen tissue section. It will be appreciated that the methods to detect human NK cells can also make use of additional staining reagents (e.g. antibodies) to identify other cells (e.g. non-NK cells), to identify markers present on NK cells, for example to identify subpopulations of NK cells, or identify other proteins expressed by the NK cells.

In one embodiment the disclosure provides an antibody binds an epitope present on NKp46 expressed by purified NK cells in culture and/or in frozen tissue section and/or recombinant NKp46 polypeptide, wherein the epitope is also present on (i.e. is a common antigenic determinant shared with) formalin fixed NK cells.

In one embodiment the disclosure provides an antibody that competes for binding to the same NKp46 epitope (e.g. as present on a NKp46 polypeptide, or as present on NKp46 expressing cells in culture, in a frozen cell pellet and/or in a paraffin embedded cell pellet) as monoclonal antibody 8E5B. Optionally, the antibody is a human antibody or a mouse antibody. Optionally the antibody is selected from a library of antibodies, e.g. a phage display library. In one embodiment, the antibody is chimeric, e.g. contains a non-murine, optionally a human, constant region. In another embodiment, the antibody does not substantially bind to any non-NKp46 superfamily IgSF receptor family members. In one embodiment, the antibody lacks an Fc domain (e.g. a F(ab)'2 fragment) or comprises an Fc domain that does not substantially bind to a human Fcγ receptor, e.g. CD16. In one embodiment, the antibody does not substantially bind to a cell not expressing NKp46 but expressing one or more members of the human Immunoglobulin superfamily IgSF receptor family, in a paraffin-embedded cell pellet. In another embodiment, the antibody comprises a light chain comprising one, two or all three CDRs of the 8E5B light chain variable region sequence of SEQ ID NO: 2. In another embodiment, the antibody comprises a heavy chain comprising one, two or all three CDRs of the 8E5B heavy chain variable region sequence of SEQ ID NO: 3. In another embodiment, the antibody comprises a light chain having a CDR comprising an amino acid sequence of any one of SEQ ID NOS: 4 to 6. In another embodiment, the antibody comprises a heavy chain having a CDR comprising an amino acid sequence of any one of SEQ ID NOS: 7 to 9. In another embodiment, the antibody is 8E5B or a fragment or derivative thereof. In another embodiment, the antibody comprises a light chain variable region sequence of SEQ ID NO: 2. In another embodiment, the antibody comprises a heavy chain variable region sequence of SEQ ID NO: 3.

In one embodiment, the antibody is an antibody fragment selected from Fab, Fab', Fab'-SH, F(ab')$_2$, Fv, diabodies, single-chain antibody fragment, or a multispecific antibody comprising multiple different antibody fragments. In another embodiment, the antibody is conjugated or covalently bound to a detectable moiety.

In one embodiment the disclosure provides kits comprising any of the anti-NKp46 antibodies, preferably together with instructions for their use, e.g., according to the therapeutic or diagnostic methods provided herein. In one embodiment, the kit further comprises a labeled secondary antibody that specifically recognizes the primary anti-NKp46 antibodies. In one such embodiment, the secondary antibody is conjugated to HRP or AP. In another embodiment, the HRP or AP is conjugated to a polymer.

In one embodiment the disclosure provides a cell producing an anti-NKp46 antibody disclosed herein, e.g., a cell producing an anti-NKp46 antibody screened by selection for binding to an antigen that comprises the NKp46 epitope specifically recognized by the 8E5B antibody. In one embodiment, the cell is clone 8E5B. In a related aspect, the present invention provides a hybridoma comprising: a) a B cell from a non-human mammalian host that has been immunized with an NKp46 polypeptide and screened by selection on an antigen that comprises the NKp46 epitope specifically recognized by the 8E5B antibody, fused to b) an immortalized cell, wherein the hybridoma produces a monoclonal antibody that specifically binds to the epitope. In one embodiment the antigen is expressed by cells in a paraffin embedded cell pellet.

In one embodiment of either of these aspects, the monoclonal antibody binds to the same epitope as antibody 8E5B.

In one embodiment the disclosure provides a method of producing an antibody that specifically binds to NKp46 in paraffin-embedded tissues, said method comprising the steps of: a) providing a plurality of candidate antibodies; and b) preparing or selecting antibodies from said plurality that bind to a NKp46 polypeptide expressed by cells in a paraffin embedded cell sample, optionally preparing or selecting antibodies from said plurality that compete for binding to a NKp46 polypeptide expressed by paraffin embedded cells with antibody 8E5B.

In one embodiment the disclosure provides a method of producing an antibody that specifically binds to NKp46 in paraffin-embedded tissues, said method comprising the steps of: a) providing a plurality of candidate monoclonal antibodies; and b) preparing or selecting antibodies from said plurality that bind to a NKp46 polypeptide expressed by a cell in a paraffin embedded cell pellet.

In another aspect, the present invention provides a method of detecting NK cells in a formalin-treated and/or paraffin-embedded tissue sample, the method comprising the steps of a) contacting the tissue sample with an anti-NKp46 antibody; and b) detecting the presence of the bound antibody in the tissue sample. If NKp46 is detected, the sample can be determined as comprising NK cells, e.g. tissue-infiltrating or tumor-infiltrating NK cells. In one embodiment, the anti-NKp46 antibody binds to an epitope on NKp46 that is present on NK cells in culture and that remains present on cells that have been formalin treated and/or preserved in a paraffin-embedded cell pellet.

In one embodiment the disclosure provides in vitro method of detecting tissue infiltrating human NK cells (e.g. tissue infiltrating human CD56$^{bright}$ NK cells) within a sample from a human individual, said method comprising providing a paraffin-embedded sample from an individual, and detecting tissue infiltrating NK cells in said sample using a monoclonal antibody that specifically binds to a human NK cell lineage specific polypeptide in paraffin-embedded tissue samples, wherein a detection of the NK cell lineage specific polypeptide indicates the presence of tissue infiltrating NK cells. Optionally, the method further comprises detecting in said sample a second polypeptide using a monoclonal antibody that specifically binds to the second polypeptide in paraffin-embedded tissue samples, wherein the second polypeptide is a lineage non-specific, polypeptide expressed by NK cells. Optionally, the monoclonal antibody is capable of detecting $CD56^{dim}$ and $CD56^{bright}$ NK cells. Optionally, NKp46 is the sole marker used to determine the lineage of NK cells.

In one embodiment, the present invention provides a method of detecting the presence and/or level of NKp46 and/or NK cells in a tissue sample, the method comprising the steps of a) contacting the tissue sample with an anti-NKp46 antibody described herein; and b) detecting the presence of the bound antibody in the tissue sample. Optionally, the tissue sample is a formalin-treated and/or paraffin-embedded tissue sample, cultured cells, a biological sample that comprises a biological fluid (for example serum, lymph, blood, synovial fluid), cell sample, or tissue sample (for example bone marrow or tissue biopsy including mucosal tissue such as from the gut, gut lamina propria, or lungs). Optionally, the tissue sample is from an individual suffering from a cancer, inflammatory or autoimmune disorder or infectious disease. In one embodiment, the method further comprises a step (c): if expression of NKp46 is detected, administering to the patient an immunotherapeutic agent. In one embodiment, the immunotherapeutic agent is an agent that is capable of directly modulating the activity of an immune cell, optionally an NK cell, optionally a T cell, optionally an NK cell and a T cell, e.g. by binding to a cell surface receptor on the immune cell. In one embodiment, the immunotherapeutic agent is an agent that is capable of indirectly modulating the activity of an immune cell, optionally an NK cell, optionally a T cell, optionally an NK cell and a T cell, e.g. by binding to a polypeptide that is a natural ligand of a cell surface receptor on the immune cell.

In another aspect, e.g. for evaluating immune cell infiltrates (e.g. NK cells, T cells, monocytes, granulocytes, etc.) and/or polypeptides expressed by such cells, NKp46 provides a lineage-specific NK cell marker expressed by all NK cells and furthermore substantially throughout their life cycle, permitting such NK cell marker detection to be combined with detection of one or more non-lineage specific or maturation dependent markers expressed on NK cells and/or on non-NK cells. The non-lineage specific marker can be for example another IgSF member, e.g., a IgSF activating (e.g. co-stimulatory) or inhibitory receptor, notably molecules of the CD28 family such as CD28, CTLA-4, program death-1 (PD-1), the B- and T-lymphocyte attenuator (BTLA, CD272), and the inducible T-cell co-stimulator (ICOS, CD278); and their IgSF ligands belonging to the B7 family; CD80 (B7-1), CD86 (B7-2), ICOS ligand, PD-L1 (B7-H1), PD-L2 (B7-DC), B7-H3, and B7-H4 (B7x/B7-S1), or any other IgSF family member such as antigen presenting molecules, natural cytotoxicity receptors (NKp30, NKp44), co-receptors, antigen receptor accessory molecules, IgSF CAMs, cytokine receptors such as Interleukin-6 receptor or colony stimulating factor 1 receptor, growth factor receptors such as PDGFR or SCFR, c-kit, CD117 antigen, receptor tyrosine kinases/phosphatases such as Type IIa and Type IIb Receptor protein tyrosine phosphatases (RPTPs), or Ig binding receptors such as Fc receptors. In one embodiment, the marker is CD56 and/or CD16. For example, NK cells have been found to express the non-lineage specific protein PD-1 in addition to NKp46, thus one can use anti-NKp46 antibodies and anti-PD-1 antibodies to identify whether NK cells expressing PD-1 are present, e.g., in the tumor environment.

For example in one embodiment the present invention provides a method of detecting (e.g., characterizing, quantifying) NK cells in a formalin-treated and/or paraffin-embedded tissue sample from an individual, the method comprising the steps of a) contacting the tissue sample with an anti-NKp46 antibody and with an antibody that binds a non-NKp46 polypeptide (e.g. a non-lineage specific polypeptide discussed herein), optionally a non-NKp46 polypeptide capable of being expressed by NK cells; and b) detecting the presence of the bound antibodies in the tissue sample. Optionally, the tissue sample is contacted with 1, 2, 3, 4, 5, or 10 more different monoclonal antibodies that bind different non-NKp46 polypeptides. Optionally, the non-NKp46 polypeptide is a marker of a non-NK cell population, a marker of an NK sub-population, a marker associated with an NK cell maturation stage. Optionally the non-NKp46 polypeptide is a marker associated with cellular activation, inhibition, anergy/exhaustion or suppression and/or proliferation; optionally the marker is not lineage specific, optionally the marker is capable of being expressed by NK cells and T cells. Optionally the non-NKp46 polypeptide is selected from the group consisting of: an immune cell activating or inhibitory receptor, an activating receptor capable of being expressed on NK and/or T cells, an inhibitory receptor capable of being expressed on NK and/or T cells, and a cell surface polypeptide expressed by an immune cell which is targeted by a medicament (e.g. a therapeutic antibody). For example, a detection of the anti-NKp46 antibody in the sample indicates the presence of NK cells. When the non-NKp46 polypeptide is a marker of a non-NK cell population, a detection of the antibody that binds a non-NKp46 polypeptide in the sample indicates the presence of said non-NK cell population. When the non-NKp46 polypeptide is a marker of an NK cell sub-population, a detection of the antibody that binds a non-NKp46 polypeptide in the sample indicates the presence of said NK cell sub-population.

The presence of infiltrating NK and/or other cells may be used as an indicator that administering a therapeutic agent that modulates such cells may be of therapeutic benefit, as the cell population(s) (e.g. NK cells) that are modulated or targeted by the therapeutic agent are present in the relevant tissue (e.g. tumor). Thus, in one embodiment, the method further comprises a step (c): if expression of NKp46 and/or the non-NKp46 polypeptide is detected, administering to the individual an immunotherapeutic agent. In one embodiment, the immunotherapeutic agent is an agent that is capable of directly or indirectly modulating the activity of an immune cell, optionally an effector cell, optionally a NK cell, optionally a T cell, optionally an NK cell and a T cell.

When the non-NKp46 polypeptide is a marker associated with cellular activation, inhibition, anergy/exhaustion or suppression and/or proliferation, a detection of the antibody that binds a non-NKp46 polypeptide in the sample indicates the presence, respectively, of cells that are or have the potential to be activated, inhibited, anergic/exhausted or suppressed, and/or proliferating. The finding that tissue infiltrating NK and/or other cells are or have the potential to be activated, inhibited, anergic/exhausted or suppressed, and/or proliferating may be used as an indicator that administering a therapeutic agent that modulates their activation, inhibition, anergy/exhaustion, suppression, and/or proliferation may be of therapeutic benefit. Thus, in one embodiment, the method further comprises a step (c): if expression of NKp46 and/or the non-NKp46 polypeptide is detected, administering to the individual an immunotherapeutic agent capable of directly or indirectly modulating the activation, inhibition, anergy/exhaustion, suppression, and/or proliferation of an immune cell, optionally an effector cell, optionally a NK cell, optionally a T cell, optionally an NK cell and a T cell.

In another embodiment, infiltrating NK cells and optionally other infiltrating immune cells can be detected in a paraffin embedded sample using an anti-NKp46 antibody in combination with a second antibody that identifies a polypeptide targeted by a therapeutic agent. The finding that the polypeptide targeted by a therapeutic agent is present on the desired immune cells (e.g. NK cells, T cells, other immune cells and/or tumor cells), and/or that NK and/or other cells are present in desired numbers, and/or that the polypeptide is present at sufficient levels on such cells, can indicate that administration of the therapeutic (e.g. immunotherapeutic) agent may be of therapeutic benefit. In one embodiment the present invention provides a therapeutic and/or prognostic method for a therapeutic agent, the method comprising the steps of: a) contacting a formalin-treated and/or paraffin-embedded disease tissue sample from an individual having a disease (e.g. a cancer, an infectious or an inflammatory disorder) with an anti-NKp46 antibody and with an antibody that binds a polypeptide targeted by an immunotherapeutic agent (e.g. a therapeutic antibody); and b) detecting the presence of the bound antibodies in the tissue sample. A detection of anti-NKp46 antibody and of the antibody that binds a polypeptide targeted by an immunotherapeutic agent in the sample indicates that NK cells are present in the disease tissue and that the polypeptide targeted by an immunotherapeutic agent is present on cells within the disease tissue, and optionally further that the individual is suitable for (likely to benefit from) treatment with the immunotherapeutic agent. In one embodiment, the immunotherapeutic agent is an agent (e.g. an antibody comprising an Fc domain that binds a CD16 polypeptide) that is capable of mediating ADCC toward a target cell (e.g. a cell expressing the antigen bound by immunotherapeutic agent; a cancer cell). For example, a finding that NKp46-expressing cells and tumor cells expressing a tumor antigen are present in the tumor environment can indicate that an ADCC-inducing antibody that targets the tumor antigen will be capable of causing NK-cell mediated ADCC of the tumor cells. In another embodiment, the immunotherapeutic agent is a bispecific antigen binding agent such as a bispecific antibody that binds an antigen (e.g. a tumor antigen) expressed by a target cell (e.g. a tumor cell) and an NKp46 polypeptide; a finding that NKp46-expressing cells (NK cells) and cells (e.g. tumor cells) expressing the antigen (tumor antigen) are present in the tumor environment can indicate that the bispecific agent will be able to induce the NK cell-mediated lysis of the target cells. In one embodiment, the method further comprises a step (c): if expression of NKp46 and/or the polypeptide targeted by an immunotherapeutic agent is detected, administering to the individual the immunotherapeutic agent. In one embodiment, the immunotherapeutic agent is an agent that is capable of directly or indirectly modulating the activity of an immune cell, optionally an effector cell, optionally a NK cell, optionally a T cell, optionally an NK cell and a T cell.

In one embodiment, the tissue sample comprises a human tissue selected from the group consisting of cancer tissue, e.g., tissue from a cancer patient, tissue proximal to or at the periphery of a cancer, cancer adjacent tissue, adjacent non-tumorous tissue or normal adjacent tissue. In one embodiment, the tissue is from a carcinoma, melanoma or sarcoma. In one embodiment, the cancer or tumor is a carcinoma, melanoma or sarcoma.

In another embodiment, the tissue sample comprises a human tissue selected from the group consisting of inflamed tissue (e.g. from a site of inflammation in an individual having an inflammatory disorder). In another embodiment, the tissue is a tumor tissue selected from the group consisting of skin, breast, lung, esophagus, stomach, larynx, kidney, and cervix.

In one embodiment of any of the methods or compositions herein, an NK cell may be specified as being a cytotoxic and/or active NK cell, e.g., having the capacity of lysing target cells and/or enhancing the immune function of other cells.

In one embodiment of any of the methods, in step c) an immunotherapeutic agent is administered to the patient if NKp46 detected in step b) is detected at an elevated level. In another embodiment, the cancerous tissue is selected from the group consisting of breast, lung, esophagus, stomach, larynx, kidney, and cervix. In another embodiment, the tissue is colon tissue, and optionally further the patient has colorectal cancer. In another embodiment, the tissue is a melanoma.

While NKp46 is highly specific to NK cells (e.g. within non-malignant cells), certain lymphomas such as T cell lymphomas have been found to be capable of expressing NKp46. Accordingly, in any embodiment herein, a tissue sample (or a tumor or cancer) can be specified as being a sample or tissue sample (or a tumor or cancer) other than a lymphoma (or T cell lymphoma, CD4 T cell lymphoma). For example a tissue may be carcinoma or sarcoma tissue; a cancer or tumor is a carcinoma or sarcoma.

In view of the existence of certain NKp46-expressing lymphomas, in another aspect the present invention provides a method of detecting (e.g. characterizing) and/or treating an NKp46-expressing cancer, for example an NK cell or T cell lymphoma. In one aspect, provided is an in vitro method of detecting malignant NKp46-expressing cells in an individual having a lymphoma, said method comprising providing a paraffin-embedded sample from an individual having a lymphoma, and detecting malignant cells in said sample expressing NKp46 according to the method of the disclosure or using an antibody of the disclosure. Optionally, the NKp46-expressing cancer is a CTCL (e.g. Sezary Syndrome, Mycosis fungoides), a NK-LDGL, an NK/T lymphoma nasal type, a Peripheral T-Cell Lymphoma (PTCL) (e.g. an enteropathy associated T cell lymphoma (EATL), a PTCL-Not Otherwise Specified (PTCL-NOS), or an anaplastic large cell lymphoma (ALCL)), or a pre-malignant condition of a PTCL such as Celiac Disease, optionally Refractory Celiac Disease (RCD), optionally RCD type I or type II. Optionally, the method further comprises detecting in said sample a second polypeptide using a monoclonal antibody that specifically binds to the second polypeptide in paraffin-embedded tissue samples, wherein the second polypeptide is a polypeptide expressed by lymphoma cells, optionally wherein the second polypeptide is CD4 or CD30. In one aspect, the present invention provides a method of treating an individual having a lymphoma, e.g., a CTCL or a PTCL, the method comprising a) providing a formalin-treated and/or paraffin-embedded cancer sample from the individual; b) detecting NKp46 in the cancer samples; optionally a detection of NKp46 indicates the individual is suitable for treatment with an anti-NKp46 agent (e.g. an agent that depletes NKp46-expressing cells). In one aspect, the paraffin-embedded cancer sample is a paraffin-embedded cell pellet. In one aspect, the present invention provides a method of treating an individual with a cancer, the method comprising a) providing a formalin-treated and/or paraffin-embedded cancer sample from the individual; b) detecting NKp46 in the cancer samples, wherein a detection of NKp46 indicates the individual is suitable for treatment with an anti-NKp46 agent; and optionally: c) if NKp46 expression is detected in the cancer sample, administering a therapeutic agent that leads to the elimination of NKp46-expressing cells (e.g., an anti-NKp46 antibody) to the patient. In one aspect of the any of the embodiments, the cancer or lymphoma is a CTCL, Sezary Syndrome, Mycosis fungoides, a NK-LDGL, an NK/T lymphoma nasal type, a Peripheral T-Cell Lymphoma (PTCL), enteropathy associated T cell lymphoma (EATL), a PTCL-Not Otherwise Specified (PTCL-NOS), or an anaplastic large cell lymphoma (ALCL).

In any embodiment herein, binding to paraffin embedded cells or tissue sample can be assessed by detecting binding following deparaffinization of the cells or sample. In any embodiment, reference to formalin or paraffin can be replaced by any or equivalent material, e.g. as further disclosed herein.

These and additional advantageous aspects and features of the invention may be further described elsewhere herein.

BRIEF DESCRIPTION OF THE DRAWING

FIG. 3 shows mean fluorescence intensity obtained by flow cytometry after immunofluorescent staining with a PE-coupled anti-NKp46 antibody on Raji-huNKp46 Low, High and SNK6, a cell line of NK/T lymphoma which expresses NKp46 endogenously.

DETAILED DESCRIPTION OF THE INVENTION

Definitions

Figure 1:
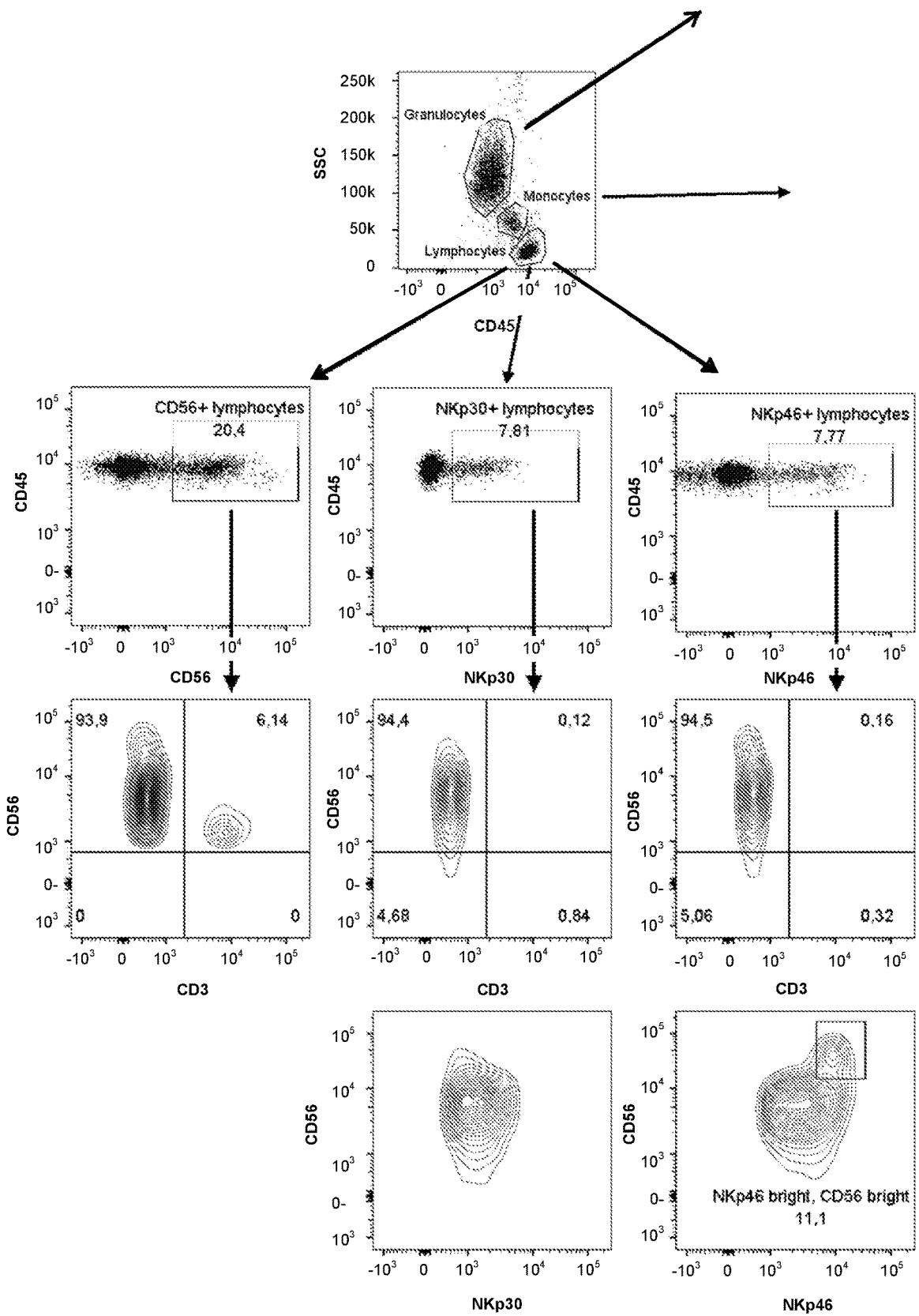
FIG. 1 shows results from staining for NKp46, illustrating that NKp46 is present on all NK cells, including $CD56^{bright}$, representing 11.1% of NKp46-positive cells, whereas NKp30 was missing on the $CD56^{bright}$ Subset. The $CD56^{bright}$ NK cell subset are numerically in the minority in peripheral blood but constitute the majority of NK cells in secondary lymphoid tissues as well as in tumor tissues.

As used herein, "paraffin-embedded sample" (or paraffin-embedded "cells", "cell pellet", "slides", or "tissues") refers to cells or tissues taken from an organism or from in vitro cell culture that have been fixed, embedded in paraffin, sectioned, deparaffinized, and transferred to a slide. It will be appreciated that fixation and paraffin embedding is a common practice that can vary in many aspects, e.g., with respect to the fixation and embedding methods used, with respect to the protocol followed, etc., and that for the purposes of the present invention any such variant method is encompassed, so long as it involves fixation of the tissue (such as by formalin treatment), embedding in paraffin or equivalent material, sectioning and transfer to a slide.

The term "biological sample" or "sample" as used herein includes but is not limited to a biological fluid (for example serum, lymph, blood), cell sample, or tissue sample (for example bone marrow or tissue biopsy including mucosal tissue such as from the gut, gut lamina propria, or lungs).

As used in the specification, "a" or "an" may mean one or more. As used in the claim(s), when used in conjunction with the word "comprising", the words "a" or "an" may mean one or more than one.

Where "comprising" is used, this can optionally be replaced by "consisting essentially of", more optionally by "consisting of".

As used herein, the term "antigen binding domain" refers to a domain comprising a three-dimensional structure capable of immunospecifically binding to an epitope. Thus, in one embodiment, said domain can comprise a hypervariable region, optionally a VH and/or VL domain of an antibody chain, optionally at least a VH domain. In another embodiment, the binding domain may comprise one, two or all three complementarity determining region (CDR) of an antibody chain. In another embodiment, the binding domain may comprise a polypeptide domain from a non-immunoglobulin scaffold.

The term "antibody" herein is used in the broadest sense and specifically includes full-length monoclonal antibodies, polyclonal antibodies, multispecific antibodies (e.g., bispecific antibodies), and antibody fragments and derivatives, so long as they exhibit the desired biological activity. Various techniques relevant to the production of antibodies are provided in, e.g., Harlow, et al., ANTIBODIES: A LABORATORY MANUAL, Cold Spring Harbor Laboratory Press, Cold Spring Harbor, N.Y., (1988). An "antibody fragment" comprises a portion of a full-length antibody, e.g. antigen-binding or variable regions thereof. Examples of antibody fragments include Fab, Fab', F(ab)$_2$, F(ab')$_2$, F(ab)$_3$, Fv (typically the VL and VH domains of a single arm of an antibody), single-chain Fv (scFv), dsFv, Fd fragments (typically the VH and CH1 domain), and dAb (typically a VH domain) fragments; VH, VL, VhH, and V-NAR domains; minibodies, diabodies, triabodies, tetrabodies, and kappa bodies (see, e.g., III et al., Protein Eng 1997; 10: 949-57); camel IgG; IgNAR; and multispecific antibody fragments formed from antibody fragments, and one or more isolated CDRs or a functional paratope, where isolated CDRs or antigen-binding residues or polypeptides can be associated or linked together so as to form a functional antibody fragment. Various types of antibody fragments have been described or reviewed in, e.g., Holliger and Hudson, Nat Biotechnol 2005; 23, 1126-1136; WO2005040219, and published U.S. Patent Applications 20050238646 and 20020161201.

The term "antibody derivative", as used herein, comprises a full-length antibody or a fragment of an antibody, e.g. comprising at least antigen-binding or variable regions thereof, wherein one or more of the amino acids are chemically modified, e.g., by alkylation, PEGylation, acylation, ester formation or amide formation or the like. This includes, but is not limited to, PEGylated antibodies, cysteine-PEGylated antibodies, and variants thereof.

The term "hypervariable region" when used herein refers to the amino acid residues of an antibody that are responsible for antigen binding. The hypervariable region generally comprises amino acid residues from a "complementarity-determining region" or "CDR" (e.g. residues 24-34 (L1), 50-56 (L2) and 89-97 (L3) in the light-chain variable domain and 31-35 (H1), 50-65 (H2) and 95-102 (H3) in the heavy-chain variable domain; Kabat et al. 1991) and/or those residues from a "hypervariable loop" (e.g. residues 26-32 (L1), 50-52 (L2) and 91-96 (L3) in the light-chain variable domain and 26-32 (H1), 53-55 (H2) and 96-101 (H3) in the heavy-chain variable domain; Chothia and Lesk, J. Mol. Biol 1987; 196:901-917). Typically, the numbering of amino acid residues in this region is performed by the method described in Kabat et al., supra. Phrases such as "Kabat position", "variable domain residue numbering as in Kabat" and "according to Kabat" herein refer to this numbering system for heavy chain variable domains or light chain variable domains. Using the Kabat numbering system, the actual linear amino acid sequence of a peptide may contain fewer or additional amino acids corresponding to a shortening of, or insertion into, a FR or CDR of the variable domain. For example, a heavy chain variable domain may include a single amino acid insert (residue 52a according to Kabat) after residue 52 of CDR H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence. The application of either definition to refer to a CDR of an antibody or variants thereof is intended to be within the scope of the terms as defined and used herein. The appropriate amino acid residues which encompass the CDRs as defined by commonly used numbering chemes are set forth below in Table 1 as a comparison. The exact residue numbers which encompass a particular CDR will vary depending on the sequence and size of the CDR. Those skilled in the art can routinely determine which residues comprise a particular CDR given the variable region amino acid sequence of the antibody.

TABLE 1

| CDR | Kabat | Chotia | AbM |
|---|---|---|---|
| HCDR1 | 31-35 | 26-32 | 26-35 |
| HCDR2 | 50-65 | 52-58 | 50-58 |
| HCDR3 | 95-102 | 95-102 | 95-102 |
| VCDR1 | 24-34 | 26-32 | 24-34 |
| VCDR2 | 60-56 | 50-52 | 50-56 |
| VCDR3 | 89-97 | 91-96 | 89-97 |

By "framework" or "FR" residues as used herein is meant the region of an antibody variable domain exclusive of those regions defined as CDRs. Each antibody variable domain framework can be further subdivided into the contiguous regions separated by the CDRs (FR1, FR2, FR3 and FR4).

By "constant region" as defined herein is meant an antibody-derived constant region that is encoded by one of the light or heavy chain immunoglobulin constant region genes. By "constant light chain" or "light chain constant region" as used herein is meant the region of an antibody encoded by the kappa (Ckappa) or lambda (Clambda) light chains. The constant light chain typically comprises a single domain, and as defined herein refers to positions 108-214 of Ckappa, or Clambda, wherein numbering is according to the EU index (Kabat et al., 1991, Sequences of Proteins of Immunological Interest, 5th Ed., United States Public Health Service, National Institutes of Health, Bethesda). By "constant heavy chain" or "heavy chain constant region" as used herein is meant the region of an antibody encoded by the mu, delta, gamma, alpha, or epsilon genes to define the antibody's isotype as IgM, IgD, IgG, IgA, or IgE, respectively. For full length IgG antibodies, the constant heavy chain, as defined herein, refers to the N-terminus of the CH1 domain to the C-terminus of the CH3 domain, thus comprising positions 118-447, wherein numbering is according to the EU index.

By "Fab" or "Fab region" as used herein is meant the polypeptide that comprises the VH, CH1, VL, and CL immunoglobulin domains. Fab may refer to this region in isolation, or this region in the context of a polypeptide, multispecific polypeptide or ABD, or any other embodiments as outlined herein.

By "single-chain Fv" or "scFv" as used herein are meant antibody fragments comprising the VH and VL domains of an antibody, wherein these domains are present in a single polypeptide chain. Generally, the Fv polypeptide further comprises a polypeptide linker between the VH and VL domains which enables the scFv to form the desired structure for antigen binding. Methods for producing scFvs are well known in the art. For a review of methods for producing scFvs see Pluckthun in The Pharmacology of Monoclonal Antibodies, vol. 113, Rosenburg and Moore eds. Springer-Verlag, New York, pp. 269-315 (1994).

By "Fv" or "Fv fragment" or "Fv region" as used herein is meant a polypeptide that comprises the VL and VH domains of a single antibody.

By "Fc" or "Fc region", as used herein is meant the polypeptide comprising the constant region of an antibody excluding the first constant region immunoglobulin domain. Thus Fc refers to the last two constant region immunoglobulin domains of IgA, IgD, and IgG, and the last three constant region immunoglobulin domains of IgE and IgM, and the flexible hinge N-terminal to these domains. For IgA and IgM, Fc may include the J chain. For IgG, Fc comprises immunoglobulin domains Cγ2 (CH2) and Cγ3 (CH3) and the hinge between Cγ1 and Cγ2. Although the boundaries of the Fc region may vary, the human IgG heavy chain Fc region is usually defined to comprise residues C226, P230 or A231 to its carboxyl-terminus, wherein the numbering is according to the EU index. Fc may refer to this region in isolation, or this region in the context of an Fc polypeptide, as described below. By "Fc polypeptide" or "Fc-derived polypeptide" as used herein is meant a polypeptide that comprises all or part of an Fc region. Fc polypeptides include but is not limited to antibodies, Fc fusions and Fc fragments.

By "variable region" as used herein is meant the region of an antibody that comprises one or more Ig domains substantially encoded by any of the VL (including Vkappa (VK) and Vlambda) and/or VH genes that make up the light chain (including kappa and lambda) and heavy chain immunoglobulin genetic loci respectively. A light or heavy chain variable region (VL or VH) consists of a "framework" or "FR" region interrupted by three hypervariable regions referred to as "complementarity determining regions" or "CDRs". The extent of the framework region and CDRs have been precisely defined, for example as in Kabat (see "Sequences of Proteins of Immunological Interest," E. Kabat et al., U.S. Department of Health and Human Services, (1983)), and as in Chothia. The framework regions of an antibody, that is the combined framework regions of the constituent light and heavy chains, serves to position and align the CDRs, which are primarily responsible for binding to an antigen.

The term "specifically binds to" means that an antibody or polypeptide can bind preferably in a competitive binding assay to the binding partner, e.g. NKp46, as assessed using either recombinant forms of the proteins, epitopes therein, or native proteins present on the surface of isolated target cells. Competitive binding assays and other methods for determining specific binding are further described below and are well known in the art.

When an antibody or polypeptide is said to "compete with" a particular monoclonal antibody, it means that the antibody or polypeptide competes with the monoclonal antibody in a binding assay using appropriate target molecules or surface expressed target molecules, for example NKp46 expressed by cells in paraffin-embedded cell pellets. For example, if a test antibody reduces the binding of 8E5B to a NKp46 polypeptide or NKp46-expressing cell in a binding assay, the antibody is said to "compete" respectively with 8E5B.

The term "affinity", as used herein, means the strength of the binding of an antibody or polypeptide to an epitope. The affinity of an antibody is given by the dissociation constant $K_D$, defined as $[Ab]\times[Ag]/[Ab-Ag]$, where [Ab-Ag] is the molar concentration of the antibody-antigen complex, [Ab] is the molar concentration of the unbound antibody and [Ag] is the molar concentration of the unbound antigen. The affinity constant $K_A$ is defined by $1/K_D$. Preferred methods for determining the affinity of mAbs can be found in Harlow, et al., Antibodies: A Laboratory Manual, Cold Spring Harbor Laboratory Press, Cold Spring Harbor, N.Y., 1988), Coligan et al., eds., Current Protocols in Immunology, Greene Publishing Assoc. and Wiley Interscience, N.Y., (1992, 1993), and Muller, Meth. Enzymol. 92:589-601 (1983), which references are entirely incorporated herein by reference. One preferred and standard method well known in the art for determining the affinity of mAbs is the use of surface plasmon resonance (SPR) screening (such as by analysis with a BIAcore™ SPR analytical device).

Within the context of this invention a "determinant" designates a site of interaction or binding on a polypeptide.

The term "epitope" refers to an antigenic determinant, and is the area or region on an antigen to which an antibody or polypeptide binds. A protein epitope may comprise amino acid residues directly involved in the binding as well as amino acid residues which are effectively blocked by the specific antigen binding antibody or peptide, i.e., amino acid residues within the "footprint" of the antibody. It is the simplest form or smallest structural area on a complex antigen molecule that can combine with e.g., an antibody or a receptor. Epitopes can be linear or conformational/structural. The term "linear epitope" is defined as an epitope composed of amino acid residues that are contiguous on the linear sequence of amino acids (primary structure). The term "conformational or structural epitope" is defined as an epitope composed of amino acid residues that are not all contiguous and thus represent separated parts of the linear sequence of amino acids that are brought into proximity to one another by folding of the molecule (secondary, tertiary and/or quaternary structures). A conformational epitope is dependent on the 3-dimensional structure. The term 'conformational' is therefore often used interchangeably with 'structural'.

By "amino acid modification" herein is meant an amino acid substitution, insertion, and/or deletion in a polypeptide sequence. An example of amino acid modification herein is a substitution. By "amino acid modification" herein is meant an amino acid substitution, insertion, and/or deletion in a polypeptide sequence. By "amino acid substitution" or "substitution" herein is meant the replacement of an amino acid at a given position in a protein sequence with another amino acid. For example, the substitution Y50W refers to a variant of a parent polypeptide, in which the tyrosine at position 50 is replaced with tryptophan. A "variant" of a polypeptide refers to a polypeptide having an amino acid sequence that is substantially identical to a reference polypeptide, typically a native or "parent" polypeptide. The polypeptide variant may possess one or more amino acid substitutions, deletions, and/or insertions at certain positions within the native amino acid sequence.

"Conservative" amino acid substitutions are those in which an amino acid residue is replaced with an amino acid residue having a side chain with similar physicochemical properties. Families of amino acid residues having similar side chains are known in the art, and include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine).

The term "identity" or "identical", when used in a relationship between the sequences of two or more polypeptides, refers to the degree of sequence relatedness between polypeptides, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related polypeptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988).

Preferred methods for determining identity are designed to give the largest match between the sequences tested. Methods of determining identity are described in publicly available computer programs. Preferred computer program methods for determining identity between two sequences include the GCG program package, including GAP (Devereux et al., Nucl. Acid. Res. 12, 387 (1984); Genetics Computer Group, University of Wisconsin, Madison, Wis.), BLASTP, BLASTN, and FASTA (Altschul et al., J. Mol. Biol. 215, 403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well known Smith Waterman algorithm may also be used to determine identity.

An "isolated" molecule is a molecule that is the predominant species in the composition wherein it is found with respect to the class of molecules to which it belongs (i.e., it makes up at least about 50% of the type of molecule in the composition and typically will make up at least about 70%, at least about 80%, at least about 85%, at least about 90%, at least about 95%, or more of the species of molecule, e.g., peptide, in the composition). Commonly, a composition of a polypeptide will exhibit 98%, 98%, or 99% homogeneity for polypeptides in the context of all present peptide species in the composition or at least with respect to substantially active peptide species in the context of proposed use.

In the context herein, "treatment" or "treating" refers to preventing, alleviating, managing, curing or reducing one or more symptoms or clinically relevant manifestations of a disease or disorder, unless contradicted by context. For example, "treatment" of a patient in whom no symptoms or clinically relevant manifestations of a disease or disorder have been identified is preventive or prophylactic therapy, whereas "treatment" of a patient in whom symptoms or clinically relevant manifestations of a disease or disorder have been identified generally does not constitute preventive or prophylactic therapy.

As used herein, "NK cells" refers to a sub-population of lymphocytes that is involved in non-conventional immunity. NK cells can be identified by virtue of certain characteristics and biological properties, notably the expression of surface antigens NKp46 (NK cell specific) and/or CD56 for human NK cells, the absence of the alpha/beta or gamma/delta TCR complex on the cell surface, the ability to bind to and kill cells that fail to express "self" MHC/HLA antigens by the activation of specific cytolytic machinery, the ability to kill tumor cells or other diseased cells that express a ligand for NK activating receptors, and the ability to release protein molecules called cytokines that stimulate or inhibit the immune response. Any of these characteristics and activities can be used to identify NK cells, using methods well known in the art. Any subpopulation of NK cells will also be encompassed by the term NK cells. Within the context herein "active" NK cells designate biologically active NK cells, including NK cells having the capacity of lysing target cells or enhancing the immune function of other cells. NK cells can be obtained by various techniques known in the art, such as isolation from blood samples, cytapheresis, tissue or cell collections, etc. Useful protocols for assays involving NK cells can be found in Natural Killer Cells Protocols (edited by Campbell K S and Colonna M). Human Press. pp. 219-238 (2000).

"NKp46" refers to a protein or polypeptide encoded by the Ncr1 gene or by a cDNA prepared from such a gene. Any naturally occurring isoform, allele or variant is encompassed by the term NKp46 polypeptide (e.g., an NKp46 polypeptide 90%, 95%, 98% or 99% identical to SEQ ID NO 1, or a contiguous sequence of at least 20, 30, 50, 100 or 200 amino acid residues thereof). The 304 amino acid residue sequence of human NKp46 (isoform a) is shown as follows:
MSSTLPALLC VGLCLSQRIS AQQQTLPKPF IWAE-PHFMVP KEKQVTICCQ GNYGAVEYQL HFEG-SLFAVD RPKPPERINK VKFYIPDMNS RMAGQYSCIY RVGELWSEPS NLLDLVVTEM YDTPTLSVHP GPEVIS-GEKV TFYCRLDTAT SMFLLLKEGR SSHVQRGYGK VQAEFPLGPV TTAHRGTYRC FGSYNNHAWS FPSEPVKLLV TGDIENTSLA PEDPTFPADT WGTYL-LTTET GLQKDHALWD HTAQNLLRMG LAFLVLVALV WFLVEDWLSR KRTRERASRA STWEGRRRLN TQTL (SEQ ID NO: 1). SEQ ID NO: 1 corresponds to NCBI accession number NP_004820, the disclosure of which is incorporated herein by reference. The human NKp46 mRNA sequence is described in NCBI accession number NM_004829, the disclosure of which is incorporated herein by reference.

As used herein, the terms "cancer antigen" and "tumor antigen" are used interchangeably and refer to antigens that are differentially expressed by cancer cells and can thereby be exploited in order to target cancer cells. Cancer antigens are antigens which can potentially stimulate apparently tumor-specific immune responses. Some of these antigens are encoded, although not necessarily expressed, by normal cells. These antigens can be characterized as those which are normally silent (i.e., not expressed) in normal cells, those that are expressed only at certain stages of differentiation and those that are temporally expressed such as embryonic and fetal antigens. Other cancer antigens are encoded by mutant cellular genes, such as oncogenes (e.g., activated ras oncogene), suppressor genes (e.g., mutant p53), fusion proteins resulting from internal deletions or chromosomal translocations. Still other cancer antigens can be encoded by viral genes such as those carried on RNA and DNA tumor viruses. The cancer antigens are usually normal cell surface antigens which are either over-expressed or expressed at abnormal times. Ideally the target antigen is expressed only on proliferative cells (e.g., tumour cells), however this is rarely observed in practice. As a result, target antigens are usually selected on the basis of differential expression between proliferative and healthy tissue. Antibodies have been raised to target specific tumour related antigens including: Receptor Tyrosine Kinase-like Orphan Receptor 1 (ROR1), Cripto, CD4, CD20, CD30, CD19, CD38, CD47, Glycoprotein NMB, CanAg, Her2 (ErbB2/Neu), CD22 (Siglec2), CD33 (Siglec3), CD79, CD138, CD171, PSCA, L1-CAM, PSMA (prostate specific membrane antigen), BCMA, CD52, CD56, CD80, CD70, E-selectin, EphB2, Melanotransferin, Mud 6 and TMEFF2. Examples of cancer antigens also include B7-H3, B7-H4, B7-H6, PD-L1, MAGE, MART-1/Melan-A, gp100, adenosine deaminase-binding protein (ADAbp), cyclophilin b, colorectal associated antigen (CRC)-C017-1A/GA733, Killer-lg Like Receptor 3DL2 (KIR3DL2), protein tyrosine kinase 7(PTK7), receptor protein tyrosine kinase 3 (TYRO-3), nectins (e.g. nectin-4), carcinoembryonic antigen (CEA) and its immunogenic epitopes CAP-1 and CAP-2, etv6, aml1, prostate specific antigen (PSA), T-cell receptor/CD3-zeta chain, MAGE-family of tumor antigens, GAGE-family of tumor antigens, anti-Mullerian hormone Type II receptor, delta-like ligand 4 (DLL4), DR5, BAGE, RAGE, LAGE-1, NAG, GnT-V, MUM-1, CDK4, MUC family, VEGF, VEGF receptors, Angiopoietin-2, PDGF, TGF-alpha, EGF, EGF receptor, a member of the human EGF-like receptor family such as HER-2/neu, HER-3, HER-4 or a heterodimeric receptor comprised of at least one HER subunit, gastrin releasing peptide receptor antigen, Muc-1, CA125, αvβ3 integrins, α5β1 integrins, αIIbβ3-integrins, PDGF beta receptor, SVE-cadherin, IL-8, hCG, IL-6, IL-6 receptor, IL-15, α-fetoprotein, E-cadherin, α-catenin, β-catenin and γ-catenin, p120ctn, PRAME, NY-ESO-1, cdc27, adenomatous polyposis coli protein (APC), fodrin, Connexin 37, Ig-idiotype, p15, gp75, GM2 and GD2 gangliosides, viral products such as human papillomavirus proteins, imp-1, P1A, EBV-encoded nuclear antigen (EBNA)-1, brain glycogen phosphorylase, SSX-1, SSX-2 (HOM-MEL-40), SSX-1, SSX-4, SSX-5, SCP-1 and CT-7, and c-erbB-2, although this is not intended to be exhaustive.

Producing Anti-NKp46 Antibodies

The antibodies of this invention specifically bind to NKp46 polypeptides, e.g., NKp46 polypeptides on the surface of human cells, particularly in formalin fixed samples such as paraffin-embedded tissue sections. The ability of the antibodies to specifically bind NKp46 polypeptides in paraffin-embedded tissue sections makes them useful for numerous applications, in particular for detecting NK cells and levels or distribution of NK cells and/or NKp46 expression for diagnostic or therapeutic purposes, as described herein. In certain, preferred embodiments, the antibodies are used to determine the presence or level of NK cells in or near tumor tissue in a sample (e.g. biopsy) taken from a patient, and, if NKp46 is detected in the tissue sample, NK cells are determined to be present.

The detection of the binding of the antibody to NKp46 can be performed in any of a number of ways. For example, the antibody can be directly labeled with a detectable moiety, e.g., a luminescent compound such as a fluorescent moiety, or with a radioactive compound, with gold, with biotin (which allows subsequent, amplified binding to avidin, e.g., avidin-AP), or with an enzyme such as alkaline phosphatase (AP) or horseradish peroxidase (HRP). Alternatively, and preferably, the binding of the antibody to the human NKp46 in the sample is assessed by using a secondary antibody that binds to the primary anti-NKp46 antibody and that itself is labeled, preferably with an enzyme such as horseradish peroxidase (HRP) or alkaline phosphatase (AP); however, it will be appreciated that the secondary antibodies can be labeled or detected using any suitable method. In a preferred embodiment, an amplification system is used to enhance the signal provided by the secondary antibody, for example the EnVision system in which the secondary antibodies are bound to a polymer (e.g., dextran) that is bound to many copies of a detectable compound or enzyme such as HRP or AP (see, e.g., Wiedorn et al. (2001) The Journal of Histochemistry & Cytochemistry, Volume 49(9): 1067-1071; Kämmerer et al., (2001) Journal of Histochemistry and Cytochemistry, Vol. 49, 623-630; the entire disclosures of which are herein incorporated by reference).

In an advantageous aspect, the invention provides an antibody that competes with monoclonal antibody 8E5B and recognizes, binds to, or has immunospecificity for substantially or essentially the same, or the same, epitope or "epitopic site" on a NKp46 molecule as monoclonal antibody 8E5B. In other embodiments, the monoclonal antibody consists of, or is a derivative or fragment of, antibody 8E5B.

It will be appreciated that, while preferred antibodies bind to the same epitope as antibody 8E5B, the present antibodies can recognize and be raised against any part of the NKp46 polypeptide. For example, any fragment of NKp46, preferably but not exclusively human NKp46, or any combination of NKp46 fragments, can be used as immunogens to raise antibodies, and the antibodies of the invention can recognize epitopes at any location within the NKp46 polypeptide, so long as they can do so on paraffin-embedded sections as described herein. Preferably, the recognized epitopes are present on the cell surface, i.e. they are accessible to antibodies present outside of the cell. Most preferably, the epitope is the epitope specifically recognized by antibody 8E5B. Further, antibodies recognizing distinct epitopes within NKp46 can be used in combination, e.g. to bind to NKp46 polypeptides with maximum efficacy and breadth among different individuals or in different tissue samples.

The antibodies of this invention may be produced by a variety of techniques known in the art. Typically, they are produced by immunization of a non-human animal, preferably a mouse, with an immunogen comprising a NKp46 polypeptide, preferably a human NKp46 polypeptide. The NKp46 polypeptide may comprise the full length sequence of a human NKp46 polypeptide, or a fragment or derivative thereof, typically an immunogenic fragment, i.e., a portion of the polypeptide comprising an epitope exposed on the surface of cells expressing a NKp46 polypeptide, preferably the epitope recognized by the 8E5B antibody. Such fragments typically contain at least about 7 consecutive amino acids of the mature polypeptide sequence, even more preferably at least about 10 consecutive amino acids thereof. Fragments typically are essentially derived from the extracellular domain of the receptor. In a preferred embodiment, the immunogen comprises a wild-type human NKp46 polypeptide in a lipid membrane, typically at the surface of a cell. In a specific embodiment, the immunogen comprises intact cells, particularly intact human cells, optionally treated or lysed. In another preferred embodiment, the polypeptide is a recombinant NKp46 polypeptide.

The step of immunizing a non-human mammal with an antigen may be carried out in any manner well known in the art for stimulating the production of antibodies in a mouse (see, for example, E. Harlow and D. Lane, Antibodies: A Laboratory Manual., Cold Spring Harbor Laboratory Press, Cold Spring Harbor, N.Y. (1988), the entire disclosure of which is herein incorporated by reference). The immunogen is suspended or dissolved in a buffer, optionally with an adjuvant, such as complete or incomplete Freund's adjuvant. Methods for determining the amount of immunogen, types of buffers and amounts of adjuvant are well known to those of skill in the art and are not limiting in any way on the present invention. These parameters may be different for different immunogens, but are easily elucidated.

Similarly, the location and frequency of immunization sufficient to stimulate the production of antibodies is also well known in the art. In a typical immunization protocol, the non-human animals are injected intraperitoneally with antigen on day 1 and again about a week later. This is followed by recall injections of the antigen around day 20, optionally with an adjuvant such as incomplete Freund's adjuvant. The recall injections are performed intravenously and may be repeated for several consecutive days. This is followed by a booster injection at day 40, either intravenously or intraperitoneally, typically without adjuvant. This protocol results in the production of antigen-specific antibody-producing B cells after about 40 days. Other protocols may also be used as long as they result in the production of B cells expressing an antibody directed to the antigen used in immunization.

For polyclonal antibody preparation, serum is obtained from an immunized non-human animal and the antibodies present therein isolated by well-known techniques. The serum may be affinity purified using any of the immunogens set forth above linked to a solid support so as to obtain antibodies that react with NKp46 polypeptides.

In an alternate embodiment, lymphocytes from a non-immunized non-human mammal are isolated, grown in vitro, and then exposed to the immunogen in cell culture. The lymphocytes are then harvested and the fusion step described below is carried out.

Splenocytes can be isolated from the immunized non-human mammal and the subsequent fusion of those splenocytes with an immortalized cell in order to form an antibody-producing hybridoma. The isolation of splenocytes from a non-human mammal is well-known in the art and typically involves removing the spleen from an anesthetized non-human mammal, cutting it into small pieces and squeezing the splenocytes from the splenic capsule through a nylon mesh of a cell strainer into an appropriate buffer so as to produce a single cell suspension. The cells are washed, centrifuged and resuspended in a buffer that lyses any red blood cells. The solution is again centrifuged and remaining lymphocytes in the pellet are finally resuspended in fresh buffer.

Once isolated and present in single cell suspension, the lymphocytes can be fused to an immortal cell line. This is typically a mouse myeloma cell line, although many other immortal cell lines useful for creating hybridomas are known in the art. Preferred murine myeloma lines include, but are not limited to, those derived from MOPC-21 and MPC-11 mouse tumors available from the Salk Institute Cell Distribution Center, San Diego, U.S.A, X63 Ag8653 and SP-2 cells available from the American Type Culture Collection, Rockville, Md. U.S.A The fusion is effected using polyethylene glycol or the like. The resulting hybridomas are then grown in selective media that contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Hybridomas are typically grown on a feeder layer of macrophages. The macrophages are preferably from littermates of the non-human mammal used to isolate splenocytes and are typically primed with incomplete Freund's adjuvant or the like several days before plating the hybridomas. Fusion methods are described in Goding, "Monoclonal Antibodies: Principles and Practice," pp. 59-103 (Academic Press, 1986), the disclosure of which is herein incorporated by reference.

The cells are allowed to grow in the selection media for sufficient time for colony formation and antibody production. This is usually between about 7 and about 14 days.

The hybridoma colonies are then assayed for the production of antibodies that specifically bind to NKp46 polypeptides, preferably the epitope specifically recognized by antibody 8E5B. The assay is typically a colorimetric ELISA-type assay, although any assay may be employed that can be adapted to the wells that the hybridomas are grown in. Other assays include radioimmunoassays or fluorescence activated cell sorting. The wells positive for the desired antibody production are examined to determine if one or more distinct colonies are present. If more than one colony is present, the cells may be re-cloned and grown to ensure that only a single cell has given rise to the colony producing the desired antibody. Typically, the antibodies will also be tested for the ability to bind to NKp46 polypeptides in paraffin-embedded tissue sections or cell pellets (see Examples). Cells that do not naturally express NKp46 can be made to express human NKp46 (e.g. by transfection with nucleic acids expressing human NKp46), prepared as a cell pellet, formalin fixed, embedded in paraffin, sectioned, deparaffinized, and transferred to a slide. Control cells not expressing NKp46 (e.g. the same cells as above but not transfected with NKp46) can be used as negative control.

Hybridomas that are confirmed to produce a monoclonal antibody of this invention can be grown up in larger amounts in an appropriate medium, such as DMEM or RPMI-1640. Alternatively, the hybridoma cells can be grown in vivo as ascites tumors in an animal. After sufficient growth to produce the desired monoclonal antibody, the growth media containing monoclonal antibody (or the ascites fluid) is separated away from the cells and the monoclonal antibody present therein is purified. Purification is typically achieved by gel electrophoresis, dialysis, chromatography using protein A or protein G-Sepharose, or an anti-mouse Ig linked to a solid support such as agarose or Sepharose beads (all described, for example, in the Antibody Purification Handbook, Biosciences, publication No. 18-1037-46, Edition AC, the disclosure of which is hereby incorporated by reference). The bound antibody is typically eluted from protein A/protein G columns by using low pH buffers (glycine or acetate buffers of pH 3.0 or less) with immediate neutralization of antibody-containing fractions. These fractions are pooled, dialyzed, and concentrated as needed.

Positive wells with a single apparent colony are typically re-cloned and re-assayed to insure only one monoclonal antibody is being detected and produced.

Antibodies may also be produced by selection of combinatorial libraries of immunoglobulins, as disclosed for instance in (Ward et al. Nature, 341 (1989) p. 544, the entire disclosure of which is herein incorporated by reference).

The identification of one or more antibodies that bind(s) to NKp46, particularly substantially or essentially the same epitope as monoclonal antibody 8E5B, can be readily determined using any one of a variety of immunological screening assays in which antibody competition can be assessed according to the methods described in the Examples, or any other suitable method. It will be understood that actually determining the epitope to which an antibody described herein binds is not in any way required to identify an antibody that binds to the same or substantially the same epitope as the monoclonal antibody described herein.

For example, where the test antibodies to be examined are obtained from different source animals, or are even of a different Ig isotype, a simple competition assay may be employed in which the control (8E5B, for example) and test antibodies are admixed (or pre-adsorbed) and applied to a sample containing NKp46 polypeptides. Protocols based upon western blotting and the use of BIACORE analysis can be used in such simple competition studies.

In certain embodiments, one pre-mixes the control antibodies (8E5B, for example) with varying amounts of the test antibodies (e.g., about 1:10 or about 1:100) for a period of time prior to applying to the NKp46 antigen sample. In other embodiments, the control and varying amounts of test antibodies can simply be admixed during exposure to the NKp46 antigen sample. As long as one can distinguish bound from free antibodies (e. g., by using separation or washing techniques to eliminate unbound antibodies) and 8E5B from the test antibodies (e. g., by using species-specific or isotype-specific secondary antibodies or by specifically labeling 8E5B with a detectable label) one can determine if the test antibodies reduce the binding of 8E5B to the antigens, indicating that the test antibody recognizes substantially the same epitope as 8E5B. The binding of the (labeled) control antibodies in the absence of a completely irrelevant antibody can serve as the control high value. The control low value can be obtained by incubating the labeled (8E5B) antibodies with unlabelled antibodies of exactly the same type (8E5B), where competition would occur and reduce binding of the labeled antibodies. In a test assay, a significant reduction in labeled antibody reactivity in the presence of a test antibody is indicative of a test antibody that recognizes substantially the same epitope, i.e., one that "cross-reacts" with the labeled (8E5B) antibody. Any test antibody that reduces the binding of 8E5B to NKp46 antigens by at least about 50%, such as at least about 60%, or more preferably at least about 70% (e. g., about 65-100%), at any ratio of 8E5B:test antibody between about 1:10 and about 1:100 is considered to be an antibody that binds to substantially the same epitope or determinant as 8E5B. Preferably, such test antibody will reduce the binding of 8E5B to the NKp46 antigen by at least about 90% (e.g., about 95%).

Competition can also be assessed by, for example, a flow cytometry test. In such a test, cells bearing a given NKp46 polypeptide can be incubated first with 8E5B, for example, and then with the test antibody labeled with a fluorochrome or biotin. The antibody is said to compete with 8E5B if the binding obtained upon preincubation with a saturating amount of 8E5B is about 80%, preferably about 50%, about 40% or less (e.g., about 30%) of the binding (as measured by mean of fluorescence) obtained by the antibody without preincubation with 8E5B. Alternatively, an antibody is said to compete with 8E5B if the binding obtained with a labeled 8E5B antibody (by a fluorochrome or biotin) on cells preincubated with a saturating amount of test antibody is about 80%, preferably about 50%, about 40%, or less (e. g., about 30%) of the binding obtained without preincubation with the antibody.

A simple competition assay in which a test antibody is pre-adsorbed and applied at saturating concentration to a surface onto which a NKp46 antigen is immobilized may also be employed. The surface in the simple competition assay is preferably a BIACORE chip (or other media suitable for surface plasmon resonance analysis). The control antibody (e.g., 8E5B) is then brought into contact with the surface at a NKp46-saturating concentration and the NKp46 and surface binding of the control antibody is measured. This binding of the control antibody is compared with the binding of the control antibody to the NKp46-containing surface in the absence of test antibody. In a test assay, a significant reduction in binding of the NKp46-containing surface by the control antibody in the presence of a test antibody indicates that the test antibody recognizes substantially the same epitope as the control antibody such that the test antibody "cross-reacts" with the control antibody. Any test antibody that reduces the binding of control (such as 8E5B) antibody to a NKp46 antigen by at least about 30% or more, preferably about 40%, can be considered to be an antibody that binds to substantially the same epitope or determinant as a control (e.g., 8E5B). Preferably, such a test antibody will reduce the binding of the control antibody (e.g., 8E5B) to the NKp46 antigen by at least about 50% (e.g., at least about 60%, at least about 70%, or more). It will be appreciated that the order of control and test antibodies can be reversed: that is, the control antibody can be first bound to the surface and the test antibody is brought into contact with the surface thereafter in a competition assay. Preferably, the antibody having higher affinity for the NKp46 antigen is bound to the surface first, as it will be expected that the decrease in binding seen for the second antibody (assuming the antibodies are cross-reacting) will be of greater magnitude. Further examples of such assays are provided in, e. g., Saunal H. and al (1995) J. Immunol. Methods 183: 33-41, the disclosure of which is incorporated herein by reference.

Preferably, monoclonal antibodies that recognize a NKp46 epitope will react with an epitope that is present on all NK cells, including on $CD56^{dim}$ and $CD56^{bright}$ NK cells, but will not significantly react with non-NK cells, e.g., immune or non-immune cells, granulocytes, monocytes, B cell, T cells, etc.

In one embodiment, the antibodies of the invention are validated in an immunoassay to test their ability to bind to NKp46-expressing cells. Preferably, the validation is performed by assessing the ability of the antibody to stain NKp46-expressing cells in a paraffin-embedded tissue section. For example, tonsil tissue samples are taken from a plurality of patients, and the ability of a given antibody to stain cells within the tissue is then assessed using standard methods well known to those in the art. To assess the binding of the antibodies to the cells, the antibodies can either be directly or indirectly labeled. When indirectly labeled, a secondary, labeled antibody is typically added. Such methods are well known to those of skill in the art and are described further elsewhere herein.

While described in the context of 8E5B for the purposes of exemplification, it will be appreciated that the herein-described immunological screening assays and other assays can also be used to identify antibodies that compete with other anti-NKp46 antibodies, so long as they also bind to NKp46 in paraffin-embedded tissue samples.

Determination of whether an antibody binds within one of the epitope regions defined above can be carried out in ways known to the person skilled in the art. As one example of such mapping/characterization methods, an epitope region for an anti-NKp46 antibody may be determined by epitope "foot-printing" using chemical modification of the exposed amines/carboxyls in the NKp46 protein. One specific example of such a foot-printing technique is the use of HXMS (hydrogen-deuterium exchange detected by mass spectrometry) wherein a hydrogen/deuterium exchange of receptor and ligand protein amide protons, binding, and back exchange occurs, wherein the backbone amide groups participating in protein binding are protected from back exchange and therefore will remain deuterated. Relevant regions can be identified at this point by peptic proteolysis, fast microbore high-performance liquid chromatography separation, and/or electrospray ionization mass spectrometry. Another example of a suitable epitope identification technique is nuclear magnetic resonance (NMR) epitope mapping, where typically the position of the signals in two-dimensional NMR spectra of the free antigen and the antigen complexed with the antigen binding peptide, such as an antibody, are compared. The antigen typically is selectively isotopically labeled with 15N so that only signals corresponding to the antigen and no signals from the antigen binding peptide are seen in the NMR-spectrum. Antigen signals originating from amino acids involved in the interaction with the antigen binding peptide typically will shift position in the spectrum of the complex compared to the spectrum of the free antigen, and the amino acids involved in the binding can be identified that way.

Epitope mapping/characterization also can be performed using mass spectrometry methods. Protease digestion techniques also can be useful in the context of epitope mapping and identification. Antigenic determinant-relevant regions/sequences can be determined by protease digestion, e.g. by using trypsin in a ratio of about 1:50 to NKp46 or o/n digestion at and pH 7-8, followed by mass spectrometry (MS) analysis for peptide identification. The peptides protected from trypsin cleavage by the anti-NKp46 binder can subsequently be identified by comparison of samples subjected to trypsin digestion and samples incubated with antibody and then subjected to digestion by e.g. trypsin (thereby revealing a footprint for the binder). Other enzymes like chymotrypsin, pepsin, etc., also or alternatively can be used in similar epitope characterization methods. Moreover, enzymatic digestion can provide a quick method for analyzing whether a potential antigenic determinant sequence is within a region of the NKp46 polypeptide that is not surface exposed and, accordingly, most likely not relevant in terms of immunogenicity/antigenicity.

Upon immunization and production of antibodies in a vertebrate or cell, particular selection steps may be performed to isolate antibodies as claimed. In this regard, in a specific embodiment, the invention also relates to methods of producing such antibodies, comprising: (a) providing a library of antibodies and/or immunizing a non-human mammal with an immunogen comprising a NKp46 polypeptide and preparing antibodies from said immunized animal; and (b) selecting antibodies from step (a) that are capable of binding said NKp46 polypeptide in a paraffin-embedded cell pellet, e.g, an FFPE cell pellet. In one embodiment, the method further comprises a step (d), selecting antibodies from (a) that are capable of competing for binding to NKp46 with antibody 8E5B.

According to an alternate embodiment, the DNA encoding an antibody that binds an epitope present on NKp46 polypeptides is isolated from the hybridoma of this invention and placed in an appropriate expression vector for transfection into an appropriate host. The host is then used for the recombinant production of the antibody, or variants thereof, such as a humanized version of that monoclonal antibody, active fragments of the antibody, chimeric antibodies comprising the antigen recognition portion of the antibody, or versions comprising a detectable moiety.

DNA encoding the monoclonal antibodies of the invention, e.g., antibody 8E5B, can be readily isolated and sequenced using conventional procedures (e.g., by using oligonucleotide probes that are capable of binding specifically to genes encoding the heavy and light chains of murine antibodies). Once isolated, the DNA can be placed into expression vectors, which are then transfected into host cells such as E. coli cells, simian COS cells, Chinese hamster ovary (CHO) cells, or myeloma cells that do not otherwise produce immunoglobulin protein, to obtain the synthesis of monoclonal antibodies in the recombinant host cells. As described elsewhere in the present specification, such DNA sequences can be modified for any of a large number of purposes, e.g., for humanizing antibodies, producing fragments or derivatives, or for modifying the sequence of the antibody, e.g., in the antigen binding site in order to optimize the binding specificity of the antibody.

Antibody 8E5B

In one aspect, the antibodies bind an antigenic determinant present on NKp46 on NK cells in FFPE cell pellets. In one aspect, the antibodies bind a common antigenic determinant present on both NKp46 on NK cells in FFPE cell pellets and NKp46 expressed at the cell surface of NK cells in culture.

In one aspect, the antibodies bind substantially the same epitope as antibody 8E5B. In one embodiment, the antibodies bind to an epitope of NKp46 that at least partially overlaps with, or includes at least one residue in, the epitope bound by antibody 8E5B. The residues bound by the antibody can be specified as being present on the surface of the NKp46 polypeptide, e.g. in a NKp46 polypeptide expressed on the surface of a cell.

Binding of anti-NKp46 antibody to cells transfected with NKp46 mutants can be measured and compared to the ability of anti-NKp46 antibody to bind wild-type NKp46 polypeptide (e.g., SEQ ID NO: 1). A reduction in binding between an anti-NKp46 antibody and a mutant NKp46 polypeptide means that there is a reduction in binding affinity (e.g., as measured by known methods such FACS testing of cells expressing a particular mutant, or by Biacore testing of binding to mutant polypeptides) and/or a reduction in the total binding capacity of the anti-NKp46 antibody (e.g., as evidenced by a decrease in Bmax in a plot of anti-NKp46 antibody concentration versus polypeptide concentration). A significant reduction in binding indicates that the mutated residue is directly involved in binding to the anti-NKp46 antibody or is in close proximity to the binding protein when the anti-NKp46 antibody is bound to NKp46.

In some embodiments, a significant reduction in binding means that the binding affinity and/or capacity between an anti-NKp46 antibody and a mutant NKp46 polypeptide is reduced by greater than 40%, greater than 50%, greater than 55%, greater than 60%, greater than 65%, greater than 70%, greater than 75%, greater than 80%, greater than 85%, greater than 90% or greater than 95% relative to binding between the antibody and a wild type NKp46 polypeptide. In certain embodiments, binding is reduced below detectable limits. In some embodiments, a significant reduction in binding is evidenced when binding of an anti-NKp46 antibody to a mutant NKp46 polypeptide is less than 50% (e.g., less than 45%, 40%, 35%, 30%, 25%, 20%, 15% or 10%) of the binding observed between the anti-NKp46 antibody and a wild-type NKp46 polypeptide.

In some embodiments, anti-NKp46 antibodies are provided that exhibit significantly lower binding for a mutant NKp46 polypeptide in which a residue in a segment comprising an amino acid residue bound by antibody 8E5B is substituted with a different amino acid.

The amino acid sequence of the heavy chain variable region of antibody 8E5B is listed as SEQ ID NO: 2, the amino acid sequence of the light chain variable region is listed as SEQ ID NO: 3. In a specific embodiment, the invention provides an antibody that binds essentially the same epitope or determinant as monoclonal antibody 8E5B; optionally the antibody comprises the hypervariable region of antibody 8E5B. In any of the embodiments herein, antibody 8E5B can be characterized by the amino acid sequences and/or nucleic acid sequences encoding it. In one embodiment, the monoclonal antibody comprises the Fab or F(ab')$_2$ portion of 8E5B. Also provided is a monoclonal antibody that comprises the heavy chain variable region of 8E5B. According to one embodiment, the monoclonal antibody comprises the three CDRs of the heavy chain variable region of 8E5B Also provided is a monoclonal antibody that further comprises the variable light chain variable region of 8E5B or one, two or three of the CDRs of the light chain variable region of 8E5B. Optionally any one or more of said light or heavy chain CDRs may contain one, two, three, four or five or more amino acid modifications (e.g. substitutions, insertions or deletions). Optionally, provided is an antibody where any of the light and/or heavy chain variable regions comprising part or all of an antigen binding region of antibody 8E5B are fused to an immunoglobulin constant region of the human IgG type, optionally a human constant region, optionally a human IgG1, IgG2, IgG3 or IgG4 isotype, optionally further comprising an amino acid substitution to reduce effector function (binding to human Fcγ receptors).

In another aspect, the invention provides an antibody, wherein the antibody comprises: a HCDR1 region of 8E5B comprising an amino acid sequence as set forth in Table A-1, or a sequence of at least 4, 5, 6, 7, 8, 9 or 10 contiguous amino acids thereof, optionally wherein one or more of these amino acids may be substituted by a different amino acid; a HCDR2 region of 8E5B comprising an amino acid sequence as set forth in Table A-1, or a sequence of at least 4, 5, 6, 7, 8, 9 or 10 contiguous amino acids thereof, optionally wherein one or more of these amino acids may be substituted by a different amino acid; a HCDR3 region of 8E5B comprising an amino acid sequence as set forth in Table A-1, or a sequence of at least 4, 5, 6, 7, 8, 9 or 10 contiguous amino acids thereof, optionally wherein one or more of these amino acids may be substituted by a different amino acid; a LCDR1 region of 8E5B comprising an amino acid sequence as set forth in Table A-2, or a sequence of at least 4, 5, 6, 7, 8, 9 or 10 contiguous amino acids thereof, optionally wherein one or more of these amino acids may be substituted by a different amino acid; a LCDR2 region of 8E5B comprising an amino acid sequence as set forth in Table A-2, or a sequence of at least 4, 5, 6, 7, 8, 9 or 10 contiguous amino acids thereof, optionally wherein one or more of these amino acids may be substituted by a different amino acid; a LCDR3 region of 8E5B comprising an amino acid sequence as set forth in Table A-2, or a sequence of at least 4, 5, 6, 7, 8, 9 or 10 contiguous amino acids thereof, optionally wherein one or more of these amino acids may be deleted or substituted by a different amino acid. The HCDR1, 2, 3 and LCDR1, 2, 3 sequences can optionally be specified as all (or each, independently) being those of the Kabat numbering system (as indicated in Table A for each CDR), those of the Chotia numbering system as indicated in Table A for each CDR), those of the IMGT numbering system as indicated in Table A for each CDR), or any other suitable numbering system.

The specified variable region and CDR sequences may comprise sequence modifications, e.g. a substitution (1, 2, 3, 4, 5, 6, 7, 8 or more sequence modifications). In one embodiment, a CDRs 1, 2 and/or 3 of the heavy and light chains comprises one, two, three or more amino acid substitutions, where the residue substituted is a residue present in a sequence of human origin. In one embodiment the substitution is a conservative modification. A conservative sequence modification refers to an amino acid modification that does not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are typically those in which an amino acid residue is replaced with an amino acid residue having a side chain with similar physicochemical properties. Specified variable region and CDR sequences may comprise one, two, three, four or more amino acid insertions, deletions or substitutions. Where substitutions are made, preferred substitutions will be conservative modifications. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g. glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g. threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family and the altered antibody can be tested for retained function (i.e., the properties set forth herein) using the assays described herein.

The sequences of the CDRs, according to IMGT, Kabat and Chothia definitions systems, have been summarized in Table A-1 and A-2 below. The sequences of the variable regions of the antibodies according to the invention are listed in Table B below (if leader sequences are present any antibody chain can be specified to start at the amino acid position immediately following the end of the leader sequence), and each CDRs underlined. In any embodiment herein, a VL or VH sequence can be specified or numbered so as to contain or lack a signal peptide or any part thereof.

TABLE A-1

| mAb | CDR definition | HCDR1 SEQ ID | Sequence | HCDR2 SEQ ID | Sequence | HCDR3 SEQ ID | Sequence |
|---|---|---|---|---|---|---|---|
| 8E5B | Kabat | 4 | DTYFH | 7 | RIDPANGN TKYDPKFH D | 9 | NRYGY |
|  | Chotia | 5 | GFNIKDT |  | PANG |  | RYG |
|  | IMGT | 6 | GFNIKDTY | 8 | IDPANGNT | 10 | AANRYGY |

TABLE A-2

| mAb | CDR definition | LCDR1 SEQ ID | Sequence | LCDR2 SEQ ID | Sequence | LCDR3 SEQ ID | Sequence |
|---|---|---|---|---|---|---|---|
| 8E5B | Kabat | 11 | RSSKSLLY INGNTHLF | 14 | RMSNLAS | 15 | MQHLEYPF T |
|  | Chotia | 12 | SKSLLYIN GNTH |  | RMS | 16 | HLEYPF |
|  | IMGT | 13 | KSLLYING NTH |  | RMS |  | MQHLEYPF T |

TABLE B

| | SEQ ID NO: | Amino Acid Sequence |
|---|---|---|
| 8E5B VH | 2 | EIQLQQSGAELVKPGASVKLSCTASGFNIKDTY FHWVKQRPEQGLEWIGRIDPANGNTKYDPKFHD KATIIADISSNTAYLQFSSLTSEDTAVYYCAAN RYGYWGQGTTLTVSS |
| 8E5B VL | 3 | DIVMTQAAPSIPVTPGESVSISCRSSKSLLYIN GNTHLFWFLQRPGQSPQLLIYRMSNLASGVPDR FSGSGSGTAFTLRISRVEAEDVGVYYCMQHLEY PFTFGSGTKLEIK |

In one embodiment, the antibodies of the invention are antibody fragments that retain their binding and/or functional properties. Fragments and derivatives of antibodies of this invention (which are encompassed by the term "antibody" or "antibodies" as used in this application, unless otherwise stated or clearly contradicted by context), preferably a 8E5B-like antibody, can be produced by techniques that are known in the art. "Fragments" comprise a portion of the intact antibody, generally the antigen binding site or variable region. Examples of antibody fragments include Fab, Fab', Fab'-SH, F(ab')$_2$, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv molecules (2) single chain polypeptides containing only one light chain variable domain, or a fragment thereof that contains the three CDRs of the light chain variable domain, without an associated heavy chain moiety and (3) single chain polypeptides containing only one heavy chain variable region, or a fragment thereof containing the three CDRs of the heavy chain variable region, without an associated light chain moiety; and multispecific antibodies formed from antibody fragments.

Preparation and Staining of FFPE Samples

The present antibodies have the particular property of being able to efficiently and specifically bind to NKp46 polypeptides present in fixed tissue or cell samples. Various methods of preparing and using such tissue preparations are well known in the art, and any suitable method or type of preparation can be used. The antibodies are further capable of binding NKp46 expressed by cells (e.g., NK cells) in culture as well as in frozen tissue sections and recombinant NKp46 polypeptide (e.g. as soluble polypeptide, NKp46-His or NKp46-Fc polypeptide).

The FFPE material is typically a tissue. FFPE tissue is a piece of tissue which is first separated from a specimen animal (e.g., human patient) by dissection or biopsy. Then, this tissue is fixed in order to prevent it from decaying or degenerating and to permit one to examine it clearly under a microscope for histological, pathological or cytological studies. Fixation is the process by which the tissue is immobilized, killed and preserved for the purpose of staining and viewing it under a microscope. Post-fixation processing makes tissue permeable to staining reagents and cross-links its macromolecules so that they are stabilized and locked in position. This fixed tissue is then embedded in the wax to allow it to be cut into thin sections and be stained with hematoxylin and eosin stain. After that, microtoming is done by cutting fine sections to study stain with antibodies under microscope.

It will be appreciated, for example, that the present antibodies can be used with any fixed cell or tissue preparation, and that they are not limited by the particular fixation or embedding method used. For example, while the most common formaldehyde-based fixation procedure involves formalin (e.g., 10%), alternative methods such as paraformaldehyde (PFA), Bouin solution (formalin/picric acid), alcohol, zinc-based solutions (for one example, see, e.g., Lykidis et al., (2007) Nucleic Acids Research, 2007, 1-10, the entire disclosure of which is herein incorporated in its entirety), and others (see, e.g., the HOPE method, Pathology Research and Practice, Volume 197, Number 12, December 2001, pp. 823-826(4), the entire disclosure of which is herein incorporated by reference). Similarly, while paraffin is preferred, other materials can be used for embedding as well, e.g., polyester wax, polyethylene glycol based formulas, glycol methacrylates, JB-4 plastics, and others. For review of methods for preparing and using tissue preparations, see, e.g., Gillespie et al., (2002) Am J Pathol. 2002 February; 160(2): 449-457; Fischer et al. CSH Protocols; 2008; Renshaw (2007), Immunohistochemistry: Methods Express Series; Bancroft (2007) Theory and Practice of Histological Techniques; and PCT patent publication no. WO06074392; the entire disclosures of which are herein incorporated by reference).

In one embodiment of the invention, the FFPE tissue is a tumor tissue, for example human tumor tissue. The tumor is particularly selected from the group of tumors of the squamous epithelium, bladder, stomach, kidneys, head, neck, colon, oesophagus, cervix, thyroid, intestine, liver, brain, prostate, urogenital tract, lymphatic system, stomach, larynx and/or lung. The tumor is furthermore particularly selected from the group of lung adenocarcinoma, small-cell lung carcinomas, pancreatic cancer, glioblastomas, colon carcinoma and breast carcinoma. In addition, preference is given to a tumor of the blood and immune system, more particularly for a tumor selected from the group of a peripheral T cell lymphoma, acute myeloid leukemia, chronic myeloid leukemia, acute lymphatic leukemia and/or chronic lymphatic leukemia. Such tumors can also be designated as cancers in the meaning of the invention.

The anti-NKp46 antibody is incubated with the FFPE material for NK cell detection. The term incubation step involves the contacting of the FFPE material with the antibody of the invention for a distinct period, which depends on the kind of material, antibody and/or antigen. The incubation process also depends on various other parameters, e.g. the sensitivity of detection, which optimization follows routine procedures known to those skilled in the art. Adding chemical solutions and/or applying physical procedures, e.g. impact of heat, can improve the accessibility of the target structures in the sample. Specific incubation products are formed as result of the incubation.

Suitable tests for the detection of formed antibody/antigen complexes are known to those skilled in the art or can be easily designed as a matter of routine. Many different types of assays are known, examples of which are set forth below. Although the assay may be any assay suitable to use anti-NKp46 mAb binding to detect and/or quantify NKp46 expression, the latter is preferably determined by means of substances specifically interacting with the primary anti-NKp46 antibody.

Thus, for example, the sample (tissue or cells) to be examined is obtained by biopsy from a biological fluid, tumor tissue (e.g., breast tumor, melanoma) or from a healthy tissue, and sections (e.g., 3 mm thick or less) and fixed using formalin or an equivalent fixation method (see supra). The time of fixation depends on the application, but can range from several hours to 24 or more hours. Following fixation, the tissue is embedded in paraffin (or equivalent material), and very thin sections (e.g., 5 microns) are cut in a microtome and then mounted onto, preferably coated, slides. The slides are then dried, e.g., air dried.

Fixed and embedded tissue sections on slides can be dried and stored indefinitely. For immunohistochemistry, the slides are deparaffinized and then rehydrated. For example, they are subjected to a series of washes with, initially, xylene, and then xylene with ethanol, and then with decreasing percentages of ethanol in water.

Before antibody staining, the tissues can be subjected to an antigen retrieval step, e.g., enzymatic or heat-based, in order to break methane bridges that form during fixation and which can mask epitopes. In a preferred embodiment, a treatment in boiling 10 mM citrate buffer, pH 6, is used.

Once the slides have been rehydrated and antigen retrieval has been ideally performed, they can be incubated with the primary antibody. First, the slides are washed with, e.g., TBS, and then, following a blocking step with, e.g., serum/BSA, the antibody can be applied. The concentration of the antibody will depend on its form (e.g., purified), its affinity, the tissue sample used, but a suitable concentration is, e.g., 1-10 µg/ml. In one embodiment, the concentration used is 10 µg/ml. The time of incubation can vary as well, but an overnight incubation is typically suitable. Following a post-antibody washing step in, e.g., TBS, the slides are then processed for detection of antibody binding.

The detection method used will depend on the antibody, tissue, etc. used, and can for example involve detection of a luminescent or otherwise visible or detectable moiety conjugated to the primary antibody, or through the use of detectable secondary antibodies. Methods of antibody detection are well known in the art and are taught, e.g., in Harlow et al., Antibodies: A Laboratory Manual, Cold Spring Harbor Laboratory Press, 1st edition (Dec. 1, 1988); Fischer et al. CSH Protocols; 2008; Renshaw (2007), Immunohistochemistry: Methods Express Series; Bancroft (2007) Theory and Practice of Histological Techniques; PCT patent publication no. WO06074392; the entire disclosure of each of which is herein incorporated in its entirety.

Many direct or indirect detection methods are known and may be adapted for use. Direct labels include fluorescent or luminescent tags, metals, dyes, radionuclides, and the like, attached to the antibody. An antibody labeled with iodine-125 ($^{125}$I) can be used. A chemiluminescence assay using a chemiluminescent antibody specific for the protein is suitable for sensitive, non-radioactive detection of protein levels. An antibody labeled with fluorochrome is also suitable. Examples of fluorochromes include, without limitation, DAPI, fluorescein, Hoechst 33258, R-phycocyanin, B-phycoerythrin, R-phycoerythrin, rhodamine, Texas red, and lissamine.

Indirect labels include various enzymes well known in the art, such as horseradish peroxidase (HRP), alkaline phosphatase (AP), β-galactosidase, urease and the like. The covalent linkage of an anti-NKp46 antibody to an enzyme may be performed by different methods, such as the coupling with glutaraldehyde. Both, the enzyme and the antibody are interlinked with glutaraldehyde via free amino groups, and the by-products of networked enzymes and antibodies are removed. In another method, the enzyme is coupled to the antibody via sugar residues if it is a glycoprotein, such as peroxidase. The enzyme is oxidized by sodium periodate and directly interlinked with amino groups of the antibody. Other enzyme containing carbohydrates can also be coupled to the antibody in this manner. Enzyme coupling may also be performed by interlinking the amino groups of the antibody with free thiol groups of an enzyme, such as β-galactosidase, using a heterobifunctional linker, such as succinimidyl 6-(N-maleimido) hexanoate. The horseradish-peroxidase detection system can be used, for example, with the chromogenic substrate tetramethylbenzidine (TMB), which yields a soluble product in the presence of hydrogen peroxide that is detectable at 450 nm. The alkaline phosphatase detection system can be used with the chromogenic substrate p-nitrophenyl phosphate, for example, which yields a soluble product readily detectable at 405 nm. Similarly, the β-galactosidase detection system can be used with the chromogenic substrate o-nitrophenyl-β-D-galactopyranoxide (ONPG), which yields a soluble product detectable at 410 nm. A urease detection system can be used with a substrate, such as urea-bromocresol purple In one embodiment, the binding of the primary antibody is detected by binding a labeled secondary antibody, preferably a secondary antibody covalently linked to an enzyme such as HRP or AP. In a particularly preferred embodiment, the signal generated by binding of the secondary antibody is amplified using any of a number of methods for amplification of antibody detection. For example, the EnVision method can be used, (see, e.g., U.S. Pat. No. 5,543,332 and European Patent no. 594,772; Kämmerer et al., (2001) Journal of Histochemistry and Cytochemistry, Vol. 49, 623-630; Wiedorn et al. (2001) The Journal of Histochemistry & Cytochemistry, Volume 49(9): 1067-1071; the entire disclosures of which are herein incorporated by reference), in which the secondary antibodies are linked to a polymer (e.g., dextran) that is itself linked to many copies of AP or HRP.

Compositions and Uses in Diagnostics, Prognostics and Therapy

As demonstrated herein, the antibodies of the invention are particularly effective at detecting NK cells within biological samples, including but not limited to those prepared as FFPE, and without non-specific staining on tissues or cells that do not express NKp46 polypeptides. The antibodies will therefore have advantages for use in the study, evaluation, diagnosis, prognosis and/or prediction of pathologies where detection of and/or localization of NK cells is of interest. For example, studies have reported favorable prognosis in patients whose tumor or tumor adjacent tissues are characterized by infiltrating NK cells.

For example, cancer in patients can be characterized or assessed using an antibody disclosed herein to assess whether or not NK cells have infiltrated the tumor, including whether or not NK cells are present outside the tumor or at the tumor periphery. In patients suffering from autoimmune or inflammatory disease, biological samples from sites of inflammation (e.g. synovial fluid) can be characterized or assessed using an antibody disclosed herein to assess whether or not NK cells are present at the site of inflammation, including whether or not NK cells are present outside the site of inflammation in other tissues of interest, e.g. at the periphery of inflammatory sites. The methods can be useful to determine whether a patient has a pathology characterized by NK cells which could be amenable to modulation by therapeutic agents that directly act on NK cells or that indirectly act on NK cells, e.g., by acting on T cells, immunosuppressive immune cells or other cells that can modulate NK cell activity, for example by producing cytokines or other signaling molecules that can modulate NK cell activity. The methods can be useful to determine whether a patient has a pathology which could be amenable to modulation by therapeutic agents that act on NK cells that are near or in the inflammatory site, e.g., by acting on NK cells so as to indirectly modulate the activity of cells involved in the pathology, for example by producing cytokines or other signaling molecules. The methods described herein can optionally further comprise administering to an individual such a therapeutic agent if it determined that the individual has a pathology which could be amenable to modulation by therapeutic agents that act on NK cells that are near or in the inflammatory site.

The antibodies described herein can be used for the detection, preferably in vitro, of the presence of NK cells cells, optionally of a pathology where NK cells are involved (e.g. having a beneficial role to ameliorate disease of having a role in exacerbating disease, e.g. in cancer, infection, inflammatory or autoimmune disorders). Such a method will typically involve contacting a biological sample (e.g. a FFPE sample, deparaffinized) from a patient with an antibody according to the invention and detecting the formation of immunological complexes resulting from the immunological reaction between the antibody and the biological sample. The complex can be detected directly by labelling the antibody according to the invention or indirectly by adding a molecule which reveals the presence of the antibody according to the invention (secondary antibody, streptavidin/biotin tag, etc.). For example, labelling can be accomplished by coupling the antibody with radioactive or fluorescent tags. These methods are well known to those skilled in the art. Accordingly, the invention also relates to the use of an antibody according to the invention for preparing a diagnostic composition that can be used for detecting the presence of NKp46-expressing cells (i.e. NK cells), optionally for detecting the presence of a pathology where NKp46-expressing cells (i.e. NK cells) are present, optionally for characterizing a cancer or other pathology, in vivo or in vitro.

In some embodiments, the antibodies of the invention will be useful for predicting cancer progression. A cancer prognosis, a prognostic for cancer or cancer progression comprises providing the forecast or prediction of (prognostic for) any one or more of the following: duration of survival of a subject susceptible to or diagnosed with a cancer, duration of recurrence-free survival, duration of progression free survival of a subject susceptible to or diagnosed with a cancer, response rate to treatment in a subject or group of subjects susceptible to or diagnosed with a cancer, and/or duration of response, degree of response, or survival following treatment in a subject. Exemplary survival endpoints include for example TTP (time to progression), PFS (progression free survival), DOR (duration of response), and OS (overall survival).

The antibodies of the invention will also be generally useful for determining whether a subject is suitable for treatment with a therapeutic agent directed to a NKp46-expressing cell, for example an agent that can deplete NKp46-expressing cells. For example, WO2007/042573 provides methods for using anti-NKp46 antibodies to eliminate cells in autoimmune disorders; WO2014/125041 provides methods for using anti-NKp46 antibodies to eliminate cells in peripheral T cell lymphomas. In another embodiment, the therapeutic agent is an antigen-binding fragment (e.g. an antibody, an antibody of the invention) that binds to or modulates (e.g. activates or inhibits) a NKp46 polypeptide on an NK cell thereby modulating the activity of the NK cell.

Advantageously, the anti-NKp46 antibodies can be used as a lineage specific, maturation independent marker to detect NK cells, and combined in with other markers (i.e. non-NKp46 markers) when analyzing a tissue sample. Other markers can include for example markers that specifically or non-specifically identify a non-NK cell population(s). The high NK cell specificity conferred by NKp46 staining permits NK cells to be distinguished from the other cell populations regardless of whether the other markers are not lineage specific and may be capable of binding NK cells as well as the other cell population. Examples of non-NK cell populations include but is not limited to any immune cell population, any cell population deriving from a hematopoietic stem cell precursor, e.g. a myeloid cell population (monocytes and macrophages, neutrophils, basophils, eosinophils, erythrocytes, megakaryocytes/platelets, dendritic cells), and lymphoid lineages (T-cells, B-cells). Other markers may also include for example markers that specifically or non-specifically identify any sub-population of any of the foregoing, e.g. $T_h1$ or $T_h2$ helper T cells, cytotoxic T cells, suppressor or regulatory T cells, M1 and M2 macrophages, and tumor infiltrating and/or tumor associated populations of any of the foregoing, e.g., tumor associated macrophages.

Other markers that can be used in combination with NKp46 also include any marker that identifies a stage of NK cell maturation (i.e. the marker is not present at all stages of NK cell maturation). Markers that can be used in combination with NKp46 may identify a desired subpopulation of NK cells, e.g. cytotoxic/granular NK cells (e.g. $CD16^{dim}$), KIR-inhibited and/or NKG2-restricted NK cells, regulatory NK cells (e.g. $CD16^{dim/-}$), peripheral NK cells, NK cells capable of infiltrating tissues/tumors (e.g. $CD56^{bright}$), desidual NK cells or memory NK cells (NKG2C+ and/or other markers).

In one embodiment, provided is an in vitro method of assessing the maturation status of tissue-infiltrating human NK cells within a sample from a human individual, said method comprising providing a paraffin-embedded sample from an individual, and detecting tissue infiltrating NK cells in said sample using a monoclonal antibody that specifically binds to a NKp46 polypeptide in paraffin-embedded tissue samples, wherein a detection of the NK cell lineage specific polypeptide indicates the presence of tissue infiltrating NK cells, and further detecting in said sample a second polypeptide using a monoclonal antibody that specifically binds to the second polypeptide in paraffin-embedded tissue samples, wherein the second polypeptide is a polypeptide capable of being expressed by NK cells that is representative of a stage of NK cell maturation.

Markers that can be used in combination with NKp46 also include any marker that is characteristic of or associated with cellular activity (activation, inhibition, proliferation, cytotoxic or regulatory potential, etc.). The markers of cellular activity may be capable of being expressed by multiple cell types, for example NK cells and non-NK cells. Combination with NKp46 permits the marker of cellular activity to be localized to NK cells and/or distinguished from NK cells. Moreover when such marker is the direct or indirect target of a therapeutic agent, the marker can be used advantageously to predict response to therapy and/or to identify or select patients for treatment with such a therapeutic agent.

Examples of other markers that can be used in combination with NKp46 include but are not limited to CD56, CD16, CD4, CD8, CD3, CD32, CD27, CD40, CD64, CD163, a NKG2 family member (e.g. NKG2D), a KIR family member, a siglec-family member, CD11b, IL-23R, IL-17, CD27, CD107, CD69, CD25, OX-40 (CD134), CD161, SCFR (CD117), GITR, NKp30, NKp44, DNAM-1, 2B4 (CD224), FoxP3, a molecule of the CD28 family such as CD28, CTLA-4, program death-1 (PD-1), the B- and T-lymphocyte attenuator (BTLA, CD272), and the inducible T-cell co-stimulator (ICOS, CD278); and their IgSF ligands belonging to the B7 family; CD80 (B7-1), CD86 (B7-2), ICOS ligand, PD-L1 (B7-H1), PD-L2 (B7-DC), B7-H3, and B7-H4 (B7x/B7-S1), or any other IgSF family member such as antigen presenting molecules, natural cytotoxicity receptors (NKp30, NKp44), co-receptors, antigen receptor accessory molecules, IgSF CAMs, cytokine receptors such as Interleukin-6 receptor or colony stimulating factor 1 receptor, growth factor receptors such as PDGFR or SCFR, c-kit, CD117 antigen, receptor tyrosine kinases/phosphatases such as Type IIa and Type IIb Receptor protein tyrosine phosphatases (RPTPs). Optionally, the non-NKp46 polypeptide is a marker of NK and/or T cell activation (e.g., CD69, a siglec-family polypeptide, NKp44, CD137, CD107, granzyme-B, CD25, CD134, ribosomal protein S6, notably phosphorylated ribosomal protein S6). Optionally, the non-NKp46 polypeptide is an activating receptor (including co-activatory receptors) expressed by NK and/or T cells (e.g., CD16, TMEM173 also known as Stimulator of interferon genes (STING), OX-40, NKG2D, NKG2E, NKG2C, KIR2DS2, DNAM-1, KIR2DS4, GITR, B7-H3, CD27, CD40, CD137, NKp30, NKp44, DNAM-1, 2B4 (CD224), or PD-1 (CD279)). Expression of activating receptors can be used to indicate cytotoxic potential of an NK cell, for example. Optionally, the non-NKp46 polypeptide is an inhibitory NK cell and/or T cell receptor (e.g. a KIR family member, a Siglec family member, NKG2A, TIGIT or CD96). Expression of activating receptors can be used to indicate NK cell inhibition, for example. Optionally, the non-NKp46 polypeptide is associated with lymphocyte exhaustion, inhibition or suppression, e.g. the exhaustion marker TIM-3, or polypeptides such as IDO, CD39 and CD73 which are associated with production of immunosuppressive metabolites. Optionally, the non-NKp46 polypeptide is a marker of cellular proliferation (e.g., Ki67)

The methods herein can also be useful to determine the profile of infiltrating immune cells in a tissue from a patient, e.g. a tumor, an inflammatory site. The methods herein can also be useful to determine whether a patient having such profile can be treated with a therapy effective in pathologies characterized by the profile. For example the method can be used to determine if a patient will respond to an immunotherapeutic agent (e.g. an antibody) in a patient having a disease characterized by infiltration of NK cells and/or characterized by NK cells in normal adjacent tissue. Determining the profile of infiltrating immune cells in a tissue from a patient can comprise assessing the presence of NK cells using an anti-NKp46 antibody, and assessing the presence of 1, 2, 3, 4, 5 or more other immune cell populations using antibodies that bind non-NKp46 polypeptides. Exemplary populations can be selected from a myeloid cell population, granulocytes, monocytes, macrophages, neutrophils, basophils, eosinophils, erythrocytes, megakaryocytes/platelets, dendritic cells, lymphoid lineages, T-cells, and B-cells.

The antibodies of the invention will be useful, for example, for assessing the immune status a subject having cancer prior to a treatment with an anti-cancer agent. The antibodies of the invention will also be useful, for example, for assessing the types of tumor-infiltrating immune cells (e.g. tumor infiltrating NK cells) in a subject having cancer prior to a treatment with an anti-cancer agent. The anti-NKp46 antibodies can be used alone or in combination with other immune cell markers to detect non NK-cell immune cell populations, e.g., CD4, CD8, CD3, CD11b, CD163, CD40, CD56, CD16, CD20, FoxP3, etc., to characterize the types and subtypes of cells present in a tumor or tumor microenvironment, at the tumor periphery, in lymph nodes, or in other tissues.

In one aspect, the present invention provides a method of treating a patient with cancer, the method comprising a) providing a formalin-treated and/or paraffin-embedded tissue sample from the patient; b) detecting NKp46 in the tissue sample (e.g. tumor tissue) using an anti-NKp46 antibody (and optionally further detecting one or more other markers, e.g. a non-lineage specific marker); and c) if NKp46 expression (optionally together with one or more other markers) is detected in the sample, administering a therapeutic agent (e.g., an immunotherapeutic agent) to the patient. In one embodiment the tissue sample comprises a cancer tissue or a cancer adjacent tissue (also referred to as adjacent non-tumorous tissue or normal adjacent tissue).

In one aspect, NK cells in cancer adjacent tissue may provide a favorable prognostic for immunotherapy response. In one aspect, the present invention provides a method of treating a patient with cancer, the method comprising a) providing a formalin-treated and/or paraffin-embedded cancer tissue sample and a cancer adjacent tissue sample from the patient; b) detecting NKp46 in the cancer and cancer adjacent tissue samples using an anti-NKp46 antibody; and c) if NKp46 expression is detected in the cancer adjacent tissue sample in the cancer tissue sample, administering a therapeutic agent (e.g., an immunotherapeutic agent) to the patient. In one embodiment, the immunotherapeutic agent is an agent that modulates the activity of cancer adjacent tissue NK cells.

Optionally, in any of these methods, a second, third or any number of further markers may be detected in order to further characterize the immune cell infiltrate prior to administration of a therapeutic agent. Characterizing the immune cell infiltrate may comprise detecting one or more non-NK cell populations, or further characterizing NK and/or other immune cells using non-lineage specific markers. Such characterization may permit a better assessment of whether the therapeutic agent is likely to be effective in the individual. For example, where the immunotherapeutic agent is an anti-tumor antigen antibody, presence of tumor infiltrating or tumor-adjacent cytotoxic T cell marker can be detected in addition to NK cells, or the presence and/or levels on cells of CD16 can be assessed. In another example, where the immunotherapeutic agent is an antibody that binds an activating or inhibitory NK or T cell receptor (or that binds a ligand of an inhibitor NK or T cells receptor) in order to increase NK and/or T cell activity, one or more markers of NK and T cell activation, proliferation, inhibition, cytotoxic potential, regulatory potential (e.g. cytokine production) or exhaustion can be detected (in addition to NKp46).

Accordingly, in one aspect, the present invention provides a method of treating a patient with cancer, the method comprising:

a) providing a formalin-treated and/or paraffin-embedded cancer tissue sample and/or a cancer adjacent tissue sample from the patient;

b) detecting NK cells in the cancer and/or cancer adjacent tissue sample using an anti-NKp46 antibody that binds NKp46 in paraffin-embedded tissue samples;

c) detecting a second polypeptide in the cancer and/or cancer adjacent tissue sample using an antibody that binds the second polypeptide in paraffin-embedded tissue samples; and d) if expression of NKp46 and/or the second polypeptide is detected in the cancer and/or cancer adjacent tissue sample, administering a therapeutic agent (e.g., an immunotherapeutic agent) to the patient.

In one embodiment, the second polypeptide is characteristic of NK and T cell activation, proliferation, inhibition, cytotoxic potential, regulatory potential (e.g. cytokine production) or exhaustion, wherein if expression of the second polypeptide is detected administering a therapeutic agent, wherein the therapeutic agent is an antibody that binds an NK and/or T cell activating receptor, an NK and/or T cell inhibitory receptor or a natural ligand of an NK and/or T cell inhibitory receptor In one embodiment, the second polypeptide is a polypeptide expressed by a population or sub-population of cells selected from the group consisting of: monocytes, macrophages, neutrophils, basophils, eosinophils, erythrocytes, dendritic cells, T-cells, $T_h1$ or $T_h2$ helper T cells, cytotoxic T cells, suppressor or regulatory T cells, M1 and M2 macrophages, tumor associated macrophages, and any other tumor infiltrating and/or tumor associated populations of any of the foregoing.

In one aspect of any embodiment herein, the immunotherapeutic agent is an agent that modulates the activity of tumor infiltrating and/or cancer adjacent tissue NK cells, optionally further tumor infiltrating and/or cancer adjacent tissue T cells. In one embodiment, the immunotherapeutic agent is an antibody that binds to a tumor antigen and is capable of inducing ADCC toward the tumor cell. Optionally, the immunotherapeutic agent binds (e.g. and activates) an activating receptor (including co-activatory receptors) expressed by NK and/or T cells (e.g., activating receptors CD16, TMEM173 also known as Stimulator of interferon genes (STING), CD40, CD27, OX-40, NKG2D, NKG2E, NKG2C, KIR2DS2, KIR2DS4, glucocorticoid-induced tumor necrosis factor receptor (GITR), CD137, NKp30, NKp44, or DNAM-1, 2B4 (CD224). Optionally, the immunotherapeutic agent binds and inhibits an inhibitory NK cell and/or T cell receptor, or a natural ligand of such an inhibitory receptor (e.g. an inhibitory KIR family member, a Siglec family member, an inhibitory NKG2 family member, an HLA natural ligand of a KIR or NKG2 family member, LAG-3, PD-1 (CD279) or its natural ligand PD-L1, TIGIT or CD96). Optionally, the immunotherapeutic agent binds inhibits a polypeptide that is associated with lymphocyte (e.g. T and/or NK cell) exhaustion, inhibition or suppression, e.g. the exhaustion marker TIM-3, or polypeptides such as indoleamine-2,3-dioxygenase (IDO), CD39 and CD73 which are associated with production of immunosuppressive metabolites. In one embodiment, the immunotherapeutic agent activates CD16, optionally wherein the agent is an agent (e.g. a full-length IgG1 antibody, a bispecific antibody) comprising an Fc domain that is bound by FcγR (e.g. human CD16) and which is capable of inducing ADCC via CD16 (e.g. via CD16 on NK cells).

In one embodiment, the second polypeptide is a polypeptide characteristic of NK and/or T cell activation (including potential for activation), proliferation, inhibition, cytotoxic potential, regulatory potential (e.g. cytokine production) or exhaustion. Optionally the polypeptide is not lineage specific. Optionally the polypeptide is a member of the IgSF superfamily. Detecting for example a marker associated with cellular activation, inhibition, anergy/exhaustion or suppression and/or proliferation may be useful as an indicator that administering a therapeutic agent that modulates cells' activation, inhibition, anergy/exhaustion, suppression, and/or proliferation may be of therapeutic benefit. For example, expression (e.g. high levels of expression) of an inhibitory receptor on NK and/or T cells may indicate that a therapeutic agent (e.g. an antibody) that binds and blocks the activity of such inhibitory receptor or binds and blocks the activity of a natural ligand thereof may be useful in treating the individual. Examples of inhibitory receptors and their ligands include, e.g., an inhibitory KIR family member, an inhibitory Siglec family member, an inhibitory NKG2 family member, an HLA natural ligand of a KIR or NKG2 family member, PD-1 (CD279) and its ligand PD-L1 and PD-L2, TIGIT or CD96 and their ligand CD155. In another example, expression (e.g. high levels of expression) of a protein in the tumor tissue which is associated with immune suppression of NK and/or T cells, such as IDO, CD39 and CD73, or expression on NK and/or T cells may indicate that a therapeutic agent (e.g. an antibody) that blocks the activity of such immune suppression process may be useful in treating the individual, and, e.g., may be administered to the individual. For example blocking anti-CD73 antibodies or blocking anti-CD39 antibodies can be administered, or a compound that inhibits IDO can be administered. If expression (e.g. high levels of expression) of a protein which is associated with anergy/exhaustion of NK and/or T cells, such as TIM-3, or expression on NK and/or T cells may indicate that that a therapeutic agent that relieves such anergy/exhaustion, for example an antibody that bind and blocks TIM-3 may be useful in treating the individual, and, e.g, may be administered to the individual. In another example, expression (e.g. high levels of expression) of an activating receptor on NK and/or T cells may indicate that such cells have activating potential and that a therapeutic agent (e.g. an antibody) that binds and stimulates or increases the activity of such activating receptor may be useful in treating the individual. Examples of activating expressed by NK and/or T cells include CD16, TMEM173 also known as Stimulator of interferon genes (STING), OX-40, NKG2D, NKG2E, NKG2C, KIR2DS2, KIR2DS4, glucocorticoid-induced tumor necrosis factor receptor (GITR), CD137, NKp30, NKp44, or DNAM-1, 2B4 (CD224). In yet another example, expression (e.g. high levels of expression) of the activating receptor CD16 on NK cells may indicate that such cells have activating potential and that an antibody that binds a tumor antigen and that can be bound by CD16 (e.g., an antibody that comprises an Fc domain) may be useful in treating the individual.

Optionally, in any of these methods, a second, third or any number of further markers may be detected in order to assess the presence and/or level of the molecular target of the therapeutic agent or a natural ligand thereof, optionally an immunotherapeutic agent. The NK-lineage specific anti-NKp46 antibody will permit NK cells that express the molecular target or a natural ligand thereof to be distinguished from other immune cells that express the molecular target or a natural ligand thereof. Such information will help to assess whether the individual is likely to benefit from treatment. The molecular target may be, for example, a protein to which the immunotherapeutic agent interacts such as CD16, a tumor antigen, an immune cell activating or inhibitory receptor, etc. In another example, the molecular target of a therapeutic agent that comprises an antibody linked to a toxic moiety (e.g. a cytotoxic drug) may be, for example, a protein to which such antibody-drug conjugate binds such as a tumor antigen. Where the agent is a blocking antibody, the molecular target may be, for example, a natural ligand of protein to which the immunotherapeutic agent interacts) is present and/or likely to lead to a therapeutic effect. For example where the immunotherapeutic agent is an anti-PD-1 antibody, the molecular target may be PD-L1 or PD-L2 on tumor and/or infiltrating immune cells. Where the immunotherapeutic agent is an ADCC-inducing anti-tumor antigen antibody, the molecular target may be CD16 on immune cells (e.g. NK cells) and/or the tumor antigen on tumor cells.

Accordingly, in one aspect, the present invention provides a method of treating a patient with cancer with a therapeutic agent, the method comprising:

a) providing a formalin-treated and/or paraffin-embedded cancer and/or cancer adjacent tissue sample from the patient;

b) detecting NK cells in the cancer and/or cancer adjacent tissue samples using an anti-NKp46 antibody that binds NKp46 in paraffin-embedded tissue samples;

c) detecting a polypeptide bound by a therapeutic agent, and/or a natural ligand thereof, in the cancer and/or cancer adjacent tissue sample using an antibody that binds the second polypeptide in paraffin-embedded cancer tissue samples; and d) if expression of (i) NK cells and/or (ii) the polypeptide bound by a therapeutic agent, and/or a natural ligand of the polypeptide, is detected in the cancer and/or cancer adjacent tissue sample, administering the therapeutic agent to the patient. In one embodiment, the therapeutic agent is an immunotherapeutic agent. In one embodiment, the immunotherapeutic agent is an agent that modulates the activity of tumor infiltrating and/or cancer adjacent tissue NK cells, optionally further tumor infiltrating and/or cancer adjacent tissue T cells.

Optionally, in any embodiment, the level of NK cell (e.g. NKp46 expressing cell) infiltration in the tumor is determined in vitro in a tumor sample taken from the patient or individual, e.g. prior to a treatment with a therapeutic agent (e.g. an immunotherapeutic agent). In one embodiment, the reference level is a value representative of the level of NKp46-expressing NK cell infiltration in tumors of a population of patients deriving clinical benefit from the treatment, e.g. with a therapeutic agent. In one embodiment, the reference level is a value representative of the level of NKp46-exressing NK cell infiltration in tumors of a population of patients deriving no clinical benefit from the treatment, e.g. with a therapeutic agent. In one embodiment, the reference level is determined in vitro in tumor samples taken prior to treatment from patients deriving (or not) clinical benefit from the treatment. In one embodiment, where the reference level is that of patient deriving no clinical benefit, the treatment (e.g. therapeutic agent) is administered to a patient having a level of NK cell infiltration that is at least 1.5-fold, at least 2-fold or at least 3-fold the reference level.

In one embodiment, the level of NK cell infiltration in the periphery of a tumor is determined in vitro in a tumor sample taken from the patient, e.g. prior to a treatment with a therapeutic agent (e.g. an immunotherapeutic agent). In one embodiment, the reference level is a value representative of the level of NK cell infiltration in the periphery of tumors of a population of patients deriving no clinical benefit from the treatment, e.g. with a therapeutic agent. In one embodiment, the reference level is determined in vitro in the periphery of tumor samples taken prior to treatment from patients deriving no clinical benefit from the treatment. In one embodiment, the treatment (e.g. therapeutic agent) is administered to a patient having a level of NK cell infiltration that is at least 1.5-fold, at least 2-fold or at least 3-fold the reference level.

The level of NK cell infiltration can be determined by any suitable method. For example the level of NK cell infiltration can be determined as the number of NK cells present in a given tissue, e.g. a tumor. In a particular embodiment, the level of NK cell infiltration is reflected by the number of NK cells per mm$^2$ of a FFPE tissue section (e.g. a section prepared from a tumor biopsy).

The present invention also provides a method for the treatment of cancer in a patient, wherein i) the level of NK cell infiltration in the tumor and/or tumor-adjacent tissue of the patient is determined in a paraffin-embedded sample prior to treatment, ii) the level of NK cell infiltration is compared to a reference level, and iii) an immunotherapeutic agent is administered to a patient having a higher level of NK cell infiltration (greater number of total NK cells or a particular NK cell subset) compared to the reference level. NK cell infiltration in the tumor and/or tumor-adjacent tissue can be determined according to any method disclosed herein.

In one embodiment, the level of NK cell infiltration in the tumor is determined in vitro in a tumor and/or tumor-adjacent tissue sample taken from the patient prior to treatment. In one embodiment, the reference level is a value representative of the level of NK cell infiltration in tumors and/or tumor-adjacent tissues of a population of patients deriving no clinical benefit from the treatment. In one embodiment, the reference level is determined in vitro in tumor and/or tumor-adjacent tissue samples taken prior to treatment from patients deriving no clinical benefit from the treatment. In one embodiment, the an immunotherapeutic agent is administered to a patient having a level of NK cell infiltration that is at least 1.5-fold, at least 2-fold or at least 3-fold the reference level.

Further provided is a method of treating cancer in a patient comprising administering an effective amount of an immunotherapeutic agent to the patient, provided that the level of NK cell infiltration in the tumor and/or tumor-adjacent tissue of the patient prior to treatment is higher than a reference level. In one embodiment, the level of NK cell infiltration in the tumor and/or tumor-adjacent tissue is the level determined in vitro in a tumor and/or tumor-adjacent tissue sample taken from the patient prior to treatment. In one embodiment, the reference level is a value representative of the level of NK cell infiltration in tumor and/or tumor-adjacent tissue of a population of patients deriving no clinical benefit from the treatment. In one embodiment, the reference level is determined in vitro in tumor and/or tumor-adjacent tissue samples taken prior to treatment from patients deriving no clinical benefit from the treatment. In one embodiment, the level of NK cell infiltration is at least 1.2-fold, at least 1.5-fold, at least 2-fold or at least 3-fold higher compared to the reference level.

Also encompassed is a diagnostic or prognostic kit, e.g., for cancer, comprising an antibody according to the invention. Optionally the kit comprises an antibody of the invention and an antibody (e.g. 1, 2, 3, 4, 5, 10 or more antibodies) that binds a non-NKp46 polypeptide, for use as a diagnostic or prognostic. Optionally the kit comprises an antibody of the invention for use as a diagnostic or prognostic, and an immunotherapeutic agent. Said kit can additionally comprise means by which to detect the immunological complex resulting from the immunological reaction between the biological sample and an antibody of the invention, in particular reagents enabling the detection of said antibody.

Diseases and conditions in which the present methods can be used include cancer, other proliferative disorders, infectious disease, or immune disorders such as inflammatory diseases and autoimmune diseases. More specifically, the methods of the present invention are utilized for the treatment of a variety of cancers and other proliferative diseases including, but not limited to, carcinoma, including that of the bladder, breast, colon, kidney, liver, lung, ovary, prostate, pancreas, stomach, cervix, thyroid and skin, including squamous cell carcinoma; hematopoietic tumors of lymphoid lineage, tumors of mesenchymal cell origin, including fibrosarcoma and rhabdomyoscarcoma; other tumors, including melanoma, seminoma, teratocarcinoma, neuroblastoma and glioma; tumors of the central and peripheral nervous system, including astrocytoma, neuroblastoma, glioma, and schwannomas; tumors origin, including fibrosarcoma, rhabdomyoscaroma, and osteosarcoma; and other tumors, including keratoacanthoma, seminoma, thyroid follicular cancer and teratocarcinoma. In preferred embodiments, the methods are used to diagnose or treat tumors selected from the group consisting of colon, melanoma, lung, esophagus, stomach, larynx, kidney, and cervix. The anti-NKp46 antibodies will be particularly useful to detect NK cells among the tumors, notably NK cells that are infiltrating the tumor or tumor adjacent tissues.

In certain embodiments, the cancer comprises malignant NKp46-expressing cells, and the present antibodies and methods are used to detect NKp46 expression in the cells. Examples of such diseases and conditions in which the present methods can be used include certain lymphomas such as CTCL, Sezary Syndrome, Mycosis fungoides, a NK-LDGL, an NK/T lymphoma nasal type, a Peripheral T-Cell Lymphoma (PTCL), enteropathy associated T cell lymphoma (EATL), a PTCL-Not Otherwise Specified (PTCL-NOS), or an anaplastic large cell lymphoma (ALCL).

The present antibodies can be included in kits, which may contain any number of antibodies and/or other compounds, e.g., 1, 2, 3, 4, 5, 6, 7, 8, 9, 10, or any other number of antibodies and/or compounds, as well as, in certain embodiments, antibodies or other diagnostic reagents for detecting the presence of immune cells in paraffin-embedded tissue samples. Such diagnostic antibodies will often be labeled, either directly or indirectly (e.g., using secondary antibodies, which are typically included in the kit, together with reagents, e.g., buffers, substrates, necessary for their detection).

Further aspects and advantages of this invention will be disclosed in the following experimental section, which should be regarded as illustrative and not limiting the scope of this application.

EXAMPLES

Example 1: NKp46 Expression on Immune Cell Populations

Expression of NKp46 was studied on different cell types and compared to other NK cell proteins, including IgSF members, notably the other natural cytotoxicity receptor (NCR) member NKp30.

Briefly, 100 μL of fresh blood from a healthy volunteer were incubated with a mix of fluorochromes-conjugated antibodies (anti-CD45, Anti-CD3, anti-CD56, anti-CD8, anti-NKp46, anti-NKp30, anti-CD19, anti-CD20) for 30 minutes at room temperature. Red blood cell were analyzed and cells were fixed using the Beckman Coulter Optilyse C reagent according to manufacturer's instructions. Samples were acquired on a BD FACS CANTO II and analyzed with Flowjo software.

Granulocytes were defined as CD45 med/SSC high cells. Monocytes as CD45high/SSC med cells and lymphocytes as CD45high/SSC low cells. Within lymphocytes, T cells were identified as CD3 positive cells and further divided in CD8 positive or CD8 negative T cells. NK cells were identified as CD3 negative, CD56 positive cells. B cells were identified as CD3 negative, CD56 negative and CD19/CD20 positive cells.

CD56, NKp30 and NKp46 stainings are overlaid to background staining obtained in the condition with only a mix of anti-CD45/CD3/CD8/CD56.

Figure 2:
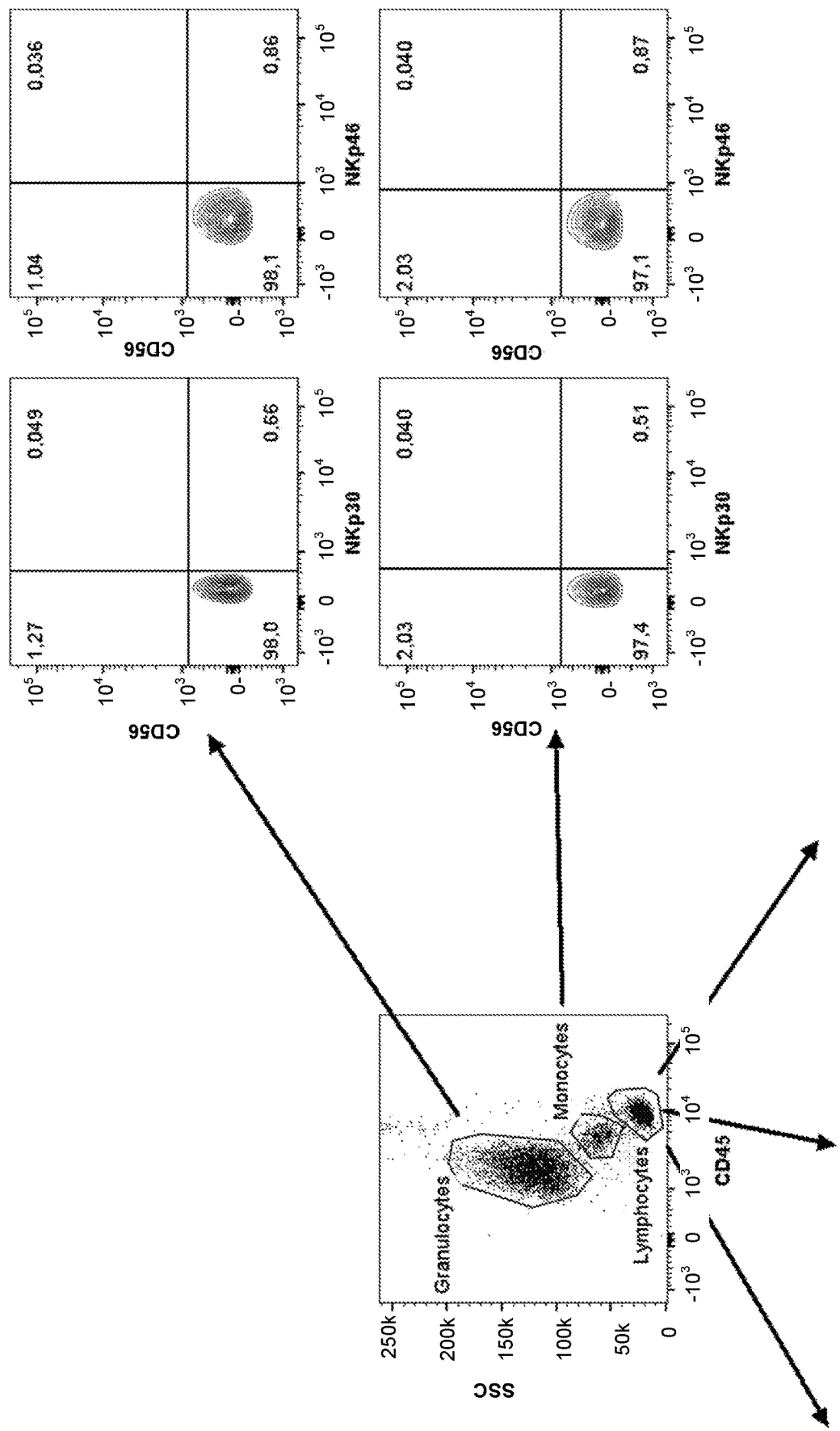
FIG. 2 shows results from staining for NKp46, illustrating that NKp46 and NKp30 were both highly specific to NK cells, without staining of granulocyte, monocytes, B cells or T cells. CD56 on the other hand is expressed on a subset T cells (CD3+).

Results for a representative donor are shown in FIGS. 1 and 2.

As shown in FIG. 2, NKp46 and NKp30 were both highly specific to NK cells, without staining of granulocyte, monocytes, B cells or T cells. CD56 on the other hand was expressed on a subset T cells representing 6% of total CD3 T cells. Interestingly, as shown in FIG. 1 (bottom two panels), NKp46 was present on all NK cells, including CD56$^{bright}$, representing 11.1% of NKp46-positive cells (FIG. 1, bottom right panel, box showing CD56$^{bright}$ subset), whereas NKp30 was missing on the CD56$^{bright}$ subset (FIG. 1, bottom left panel). The two major NK cell subsets are CD56$^{bright}$ CD16$^{dim/-}$ and CD56$^{dim}$ CD16$^{+}$, respectively. The CD56$^{bright}$ NK cell subset is numerically in the minority in peripheral blood but constitute the majority of NK cells in secondary lymphoid tissues as well as in tumor tissues. They are abundant cytokine producers and are generally only weakly cytotoxic before activation, however can become strongly cytotoxic upon activation. NKp46 therefore provides a single marker to detect NK cells and that includes the CD56$^{bright}$ subset.

Example 2: Generation of a Monoclonal Antibody for NKp46 Immunohistochemistry (IHC) Staining on Formalin Fixed Paraffin Embedded (FFPE) Samples Selection of Raji-huNKp46 Low and Raji-huNKp46 High
Raji-huNKp46 cells were generated by transduction of the Raji cell line with human NKp46. After sub-cloning of these transduced cells, two clonal populations were selected with two different expression levels High and Low. FIG. 3 illustrates the mean fluorescence intensity obtained after immunofluorescent staining by flow cytometry with a PE-coupled anti-NKp46 monoclonal antibody (Bab281, Beckman Coulter) on Raji-huNKp46 Low, High and SNK6, a cell line of NK/T lymphoma which expresses NKp46 endogenously. The PE-coupled isotype control gave no staining as expected.

Cell Fixation, Paraffin-Embedding and Sectioning
Around 20*10$^6$ cells are collected, washed in PBS1× and pelleted in a tube after centrifugation. The cells are mixed with two drops of histogel (Microm Microtech) preheated in the microwave and then put in the refrigerator to let the histogel solidify. The solidified cell pellet is put in a cassette and fixed in formalin for 2 h. After washes in PBS1×, the cassette is incubated in an Ottix shaper bath (Diapath) for dehydration of the sample and then in an Ottix plus bath for impregnation of the sample. The cassette is then incubated in paraffin (preheated at 60° C.) for 45 min (3 times). The cell pellets are embedded in paraffin using the embedding station AP280 (Microm Microtech). The paraffin blocks are cut in 5 μm-thick sections using the Microtome (Microm Microtech). These sections are unfolded on a water bath at 40° C. and then deposited on slides. The slides are dried in a stove at 60° C. then stored at room temperature until immunohistochemistry staining.

Immunization and Screening
Three BALB/c female mice (12 weeks old) were immunized with the huNKp46-Fc recombinant protein produced in house (three 50 μg injections intraperitoneally+one 10 μg final boost intravenously). The spleens of two of these mice were harvested and fused with the myeloma cell line (X63-Ag8-656) to generate hybridomas. The cells were plated in methylcellulose semi-solid medium. The hybridoma colonies were then picked manually in liquid medium. The hybridoma supernatants (SN) were first assessed for good IgG productivity. Then, around 400 hybridoma SN were screened directly by IHC on FFPE cells pellets (Raji, Raji-huNKp46 Low, Raji-huNKp46 High) with the following IHC conditions: unmasking pH8 for 30 min, incubation of pure SN for 1 h at 37° C., revelation with the anti-mouse IgG OmniMap 16 min on the Discovery$^{XT}$ automaton (Ventana). In parallel, the hybridoma cells were frozen in RNA extraction buffer for the subsequent VH and VK cloning of the positive hits in the mouse IgG1 format. The different antibodies (Abs) generated were again validated on FFPE cell pellets (Raji transfectants+SNK6 which express NKp46 endogenously) and human spleens (unmasking pH8 for 30 min, incubation of Abs at 5 and 10 μg/ml for 1 h on cells, 2 h on tissues at 37° C., revelation with OmniMap 16 min). The 8E5-B clone was selected as the best candidate to stain NKp46 in FFPE samples (specific and no background staining). Its specificity was compared with an immuno-fluorescent co-staining of NKp46 with the polyclonal anti-NKp46 Ab from R&D. The staining was validated on the same automaton on two different sites (same reagents, different batches) and tested on different tissues expressing NKp46 (spleen, lymph nodes, endometrium, placenta, ileon and colon). In addition, the staining was validated with a manual method.

Example 3: Test of 8E5-B for NKp46 IHC Staining on FFPE NK/T Lymphoma Samples

Ten formalin-fixed paraffin-embedded (FFPE) NK/T lymphoma samples were assessed for NKp46 expression with the 8E5-B antibody. The IHC staining was performed with a manual method. Unmasking was performed at 37° C. for 30 min in a PTLink module (Dako) with an EDTA buffer pH8 (Thermo Scientific). The endogenous peroxidases and then the non-specific binding sites were blocked respectively with 3% H$_2$O$_2$ (diluted in PBS1×) for 3×10 min and 5% goat serum diluted in PBS1× for 1 h. The samples were incubated with 8E5-B diluted at 5 μg/ml in PBS1× for 2 h at room temperature. 8E5B was revealed with the envision kit (Dako) for 16 min at room temperature followed by 5 min of DAB incubation. The nucleuses were counterstained with hematoxylin for 10 sec. Nine out of the ten samples tested were positive for NKp46 staining (weak to strong). The stainings with the corresponding isotype control were clean.

Example 4: 8E5-B NKp46 IHC Staining on Frozen Samples

The 8E5-B antibody was assessed for NKp46 IHC staining on frozen samples and compared to the 9E2 reference antibody from BD Pharmingen. Both antibodies were tested on frozen cell pellet (Raji, Raji-huNKp46 Low and SNK6) and human spleen sections. Briefly, the sections were incubated with 5 µg/ml of 8E5-B, 9E2 or isotype control for 1 h at room temperature. The staining was revealed with a HRP-coupled secondary antibody (Envision kit from Dako)/DAB substrate. Both antibodies tested gave a NKp46 specific staining and comparable in intensity.

Example 5: 8E5-B NKp46 Staining by Flow Cytometry

The 8E5-B antibody was assessed for NKp46 staining by flow cytometry. The Raji-huNKp46 cells were incubated 45 min at 4° C. with a dose-range of 8E5-B (30 µg/ml, 1/3 serially diluted on 12 points). The staining was revealed with an APC-coupled anti-mouse IgG secondary antibody. Results indicated that 8E5-B binds to NKp46 by flow cytometry, demonstrating that the epitope present in FFPE remains present on cells in cell culture.

Example 6: 8E5-B NKp46 Binding by Western Blot

Human NKp46-His recombinant protein (100 ng, 50 ng and 10 ng) was loaded onto an SDS-PAGE 12% gel under reducing conditions. The gel was then transferred onto an Immobilon-P membrane (Millipore, IPVH00010). The membrane was saturated for 1H with a 5% BSA, TBS-Tween 0.05% buffer. The 8E5B antibody was used at 1 µg/ml and the staining was performed for 1H. The membrane was then washed three times with the TBS-Tween buffer. The secondary antibody, a goat anti-mouse-HRP (Bethyl, A90-131P), was diluted into a 2.5% BSA, TBS-Tween 0.05% buffer (1/5000) and incubated onto the membrane for 1H. The membrane was then washed three times with the TBS-Tween buffer. The membrane was then incubated for 1 min with the revelation solution (Bio-Rad, 170-5070) and the signal was read using a Gel Imager (Bio-Rad). The huNKp46-His protein was detected by western blot using the 8E5B antibody.

The invention claimed is:

1. An antibody comprising a light chain variable region comprising the three CDRs of the 8E5B light chain variable region sequence of SEQ ID NO: 2 and a heavy chain variable region comprising the three CDRs of the 8E5B heavy chain variable region sequence of SEQ ID NO: 3.

2. The antibody of claim 1, wherein the antibody is antigen-binding fragment of said antibody.

3. The antibody of claim 1, wherein the antibody binds to NKp46-positive cells that have been prepared as a paraffin-embedded cell pellet, but does not bind to NKp46-negative cells that have been prepared as a paraffin-embedded cell pellet.

4. The antibody of claim 1, wherein antibody is conjugated or covalently bound to a detectable moiety.

5. A kit comprising the antibody of claim 1, and a labeled secondary antibody that specifically recognizes the antibody.

* * * * *

```
                         SEQUENCE LISTING

<160> NUMBER OF SEQ ID NOS: 16

<210> SEQ ID NO 1
<211> LENGTH: 304
<212> TYPE: PRT
<213> ORGANISM: homo sapiens

<400> SEQUENCE: 1

Met Ser Ser Thr Leu Pro Ala Leu Leu Cys Val Gly Leu Cys Leu Ser
1               5                   10                  15

Gln Arg Ile Ser Ala Gln Gln Gln Thr Leu Pro Lys Pro Phe Ile Trp
            20                  25                  30

Ala Glu Pro His Phe Met Val Pro Lys Glu Lys Gln Val Thr Ile Cys
        35                  40                  45

Cys Gln Gly Asn Tyr Gly Ala Val Glu Tyr Gln Leu His Phe Glu Gly
    50                  55                  60

Ser Leu Phe Ala Val Asp Arg Pro Lys Pro Pro Glu Arg Ile Asn Lys
65                  70                  75                  80

Val Lys Phe Tyr Ile Pro Asp Met Asn Ser Arg Met Ala Gly Gln Tyr
                85                  90                  95

Ser Cys Ile Tyr Arg Val Gly Glu Leu Trp Ser Glu Pro Ser Asn Leu
            100                 105                 110

Leu Asp Leu Val Val Thr Glu Met Tyr Asp Thr Pro Thr Leu Ser Val
        115                 120                 125

His Pro Gly Pro Glu Val Ile Ser Gly Glu Lys Val Thr Phe Tyr Cys
    130                 135                 140

Arg Leu Asp Thr Ala Thr Ser Met Phe Leu Leu Leu Lys Glu Gly Arg
145                 150                 155                 160

Ser Ser His Val Gln Arg Gly Tyr Gly Lys Val Gln Ala Glu Phe Pro
                165                 170                 175

Leu Gly Pro Val Thr Thr Ala His Arg Gly Thr Tyr Arg Cys Phe Gly
            180                 185                 190

Ser Tyr Asn Asn His Ala Trp Ser Phe Pro Ser Glu Pro Val Lys Leu
        195                 200                 205

Leu Val Thr Gly Asp Ile Glu Asn Thr Ser Leu Ala Pro Glu Asp Pro
    210                 215                 220

Thr Phe Pro Ala Asp Thr Trp Gly Thr Tyr Leu Leu Thr Thr Glu Thr
```

```
                225                 230                 235                 240
Gly Leu Gln Lys Asp His Ala Leu Trp Asp His Thr Ala Gln Asn Leu
                245                 250                 255

Leu Arg Met Gly Leu Ala Phe Leu Val Leu Ala Leu Val Trp Phe
            260                 265                 270

Leu Val Glu Asp Trp Leu Ser Arg Lys Arg Thr Arg Glu Arg Ala Ser
            275                 280                 285

Arg Ala Ser Thr Trp Glu Gly Arg Arg Leu Asn Thr Gln Thr Leu
            290                 295                 300

<210> SEQ ID NO 2
<211> LENGTH: 114
<212> TYPE: PRT
<213> ORGANISM: mus musculus

<400> SEQUENCE: 2

Glu Ile Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Phe His Trp Val Lys Gln Arg Pro Glu Gln Gly Leu Glu Trp Ile
        35                  40                  45

Gly Arg Ile Asp Pro Ala Asn Gly Asn Thr Lys Tyr Asp Pro Lys Phe
    50                  55                  60

His Asp Lys Ala Thr Ile Ile Ala Asp Ile Ser Ser Asn Thr Ala Tyr
65                  70                  75                  80

Leu Gln Phe Ser Ser Leu Thr Ser Glu Asp Thr Ala Val Tyr Tyr Cys
                85                  90                  95

Ala Ala Asn Arg Tyr Gly Tyr Trp Gly Gln Gly Thr Thr Leu Thr Val
            100                 105                 110

Ser Ser

<210> SEQ ID NO 3
<211> LENGTH: 112
<212> TYPE: PRT
<213> ORGANISM: mus musculus

<400> SEQUENCE: 3

Asp Ile Val Met Thr Gln Ala Ala Pro Ser Ile Pro Val Thr Pro Gly
1               5                   10                  15

Glu Ser Val Ser Ile Ser Cys Arg Ser Ser Lys Ser Leu Leu Tyr Ile
            20                  25                  30

Asn Gly Asn Thr His Leu Phe Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Ser Gly Thr Lys Leu Glu Ile Lys
            100                 105                 110

<210> SEQ ID NO 4
<211> LENGTH: 5
<212> TYPE: PRT
<213> ORGANISM: mus musculus
```

-continued

<400> SEQUENCE: 4

Asp Thr Tyr Phe His
1               5

<210> SEQ ID NO 5
<211> LENGTH: 7
<212> TYPE: PRT
<213> ORGANISM: Mus musculus

<400> SEQUENCE: 5

Gly Phe Asn Ile Lys Asp Thr
1               5

<210> SEQ ID NO 6
<211> LENGTH: 8
<212> TYPE: PRT
<213> ORGANISM: mus musculus

<400> SEQUENCE: 6

Gly Phe Asn Ile Lys Asp Thr Tyr
1               5

<210> SEQ ID NO 7
<211> LENGTH: 17
<212> TYPE: PRT
<213> ORGANISM: mus musculus

<400> SEQUENCE: 7

Arg Ile Asp Pro Ala Asn Gly Asn Thr Lys Tyr Asp Pro Lys Phe His
1               5                   10                  15

Asp

<210> SEQ ID NO 8
<211> LENGTH: 8
<212> TYPE: PRT
<213> ORGANISM: mus musculus

<400> SEQUENCE: 8

Ile Asp Pro Ala Asn Gly Asn Thr
1               5

<210> SEQ ID NO 9
<211> LENGTH: 5
<212> TYPE: PRT
<213> ORGANISM: mus musculus

<400> SEQUENCE: 9

Asn Arg Tyr Gly Tyr
1               5

<210> SEQ ID NO 10
<211> LENGTH: 7
<212> TYPE: PRT
<213> ORGANISM: mus musculus

<400> SEQUENCE: 10

Ala Ala Asn Arg Tyr Gly Tyr
1               5

<210> SEQ ID NO 11
<211> LENGTH: 16
<212> TYPE: PRT
<213> ORGANISM: mus musculus

```
<400> SEQUENCE: 11

Arg Ser Ser Lys Ser Leu Leu Tyr Ile Asn Gly Asn Thr His Leu Phe
1               5                   10                  15

<210> SEQ ID NO 12
<211> LENGTH: 12
<212> TYPE: PRT
<213> ORGANISM: mus musculus

<400> SEQUENCE: 12

Ser Lys Ser Leu Leu Tyr Ile Asn Gly Asn Thr His
1               5                   10

<210> SEQ ID NO 13
<211> LENGTH: 11
<212> TYPE: PRT
<213> ORGANISM: mus musculus

<400> SEQUENCE: 13

Lys Ser Leu Leu Tyr Ile Asn Gly Asn Thr His
1               5                   10

<210> SEQ ID NO 14
<211> LENGTH: 7
<212> TYPE: PRT
<213> ORGANISM: mus musculus

<400> SEQUENCE: 14

Arg Met Ser Asn Leu Ala Ser
1               5

<210> SEQ ID NO 15
<211> LENGTH: 9
<212> TYPE: PRT
<213> ORGANISM: mus musculus

<400> SEQUENCE: 15

Met Gln His Leu Glu Tyr Pro Phe Thr
1               5

<210> SEQ ID NO 16
<211> LENGTH: 6
<212> TYPE: PRT
<213> ORGANISM: mus musculus

<400> SEQUENCE: 16

His Leu Glu Tyr Pro Phe
1               5
```